(12) United States Patent
Kurtzman et al.

(10) Patent No.: US 12,227,582 B2
(45) Date of Patent: Feb. 18, 2025

(54) CD137 AGONIST ANTIBODIES AND USES THEREOF

(71) Applicant: QLSF BIOTHERAPEUTICS INC., South San Francisco, CA (US)

(72) Inventors: Aaron Kurtzman, South San Francisco, CA (US); Hieu Tran, South San Francisco, CA (US); Shihao Chen, South San Francisco, CA (US)

(73) Assignee: QLSF BIOTHERAPEUTICS INC., South San Francisco, CA (US)

(*) Notice: Subject to any disclaimer, the term of this patent is extended or adjusted under 35 U.S.C. 154(b) by 909 days.

(21) Appl. No.: 17/275,153

(22) PCT Filed: Jan. 2, 2020

(86) PCT No.: PCT/US2020/012080
§ 371 (c)(1),
(2) Date: Mar. 10, 2021

(87) PCT Pub. No.: WO2020/142624
PCT Pub. Date: Jul. 9, 2020

(65) Prior Publication Data
US 2022/0064314 A1   Mar. 3, 2022

Related U.S. Application Data

(60) Provisional application No. 62/787,509, filed on Jan. 2, 2019.

(51) Int. Cl.
| C07K 16/28 | (2006.01) |
| A61K 47/68 | (2017.01) |
| A61P 35/00 | (2006.01) |

(52) U.S. Cl.
CPC ...... *C07K 16/2878* (2013.01); *A61K 47/6849* (2017.08); *A61P 35/00* (2018.01); *C07K 2317/24* (2013.01); *C07K 2317/75* (2013.01); *C07K 2317/92* (2013.01)

(58) Field of Classification Search
CPC ............ C07K 16/2878; C07K 2317/75; C07K 2317/73; A61P 35/00; A61K 2039/505
See application file for complete search history.

(56) References Cited

U.S. PATENT DOCUMENTS

| 2011/0104049 A1 | 5/2011 | Strome et al. |
| 2013/0149301 A1 | 6/2013 | Meade |
| 2016/0244528 A1 | 8/2016 | Gray et al. |
| 2016/0368998 A1 | 12/2016 | Jure-Kunkel et al. |
| 2018/0282422 A1 | 10/2018 | Xu et al. |
| 2018/0344870 A1* | 12/2018 | Xiao ............... C12N 15/79 |

FOREIGN PATENT DOCUMENTS

| WO | 2004055513 A2 | 7/2004 |
| WO | 2018091740 A2 | 5/2018 |
| WO | 2018098370 A1 | 5/2018 |
| WO | 2018127787 A1 | 7/2018 |

OTHER PUBLICATIONS

Vanderwaal et al (Heterogeneity in pathogen transmission: mechanisms and methodology, https://doi.org/10.1111/1365-2435.12645 (2016)) (Year: 2016).*
American Cancer Society (Can Cancer be Cured?, American Cancer Society, retrieved from: https://www.cancer.org/cancer/understanding-cancer/can-cancer-be-cured.html)) (Year: 2021).*
Allison et al., Heterogeneity and Cancer, retrieved from: https://www.cancernetwork.com/view/heterogeneity-and-cancer (2014)) (Year: 2014).*
Mariuzza (Annu. Rev. Biophys. Biophys. Chem., 16: 139-159, 1987) (Year: 1987).*
McCarthy et al. (J. Immunol. Methods, 251(1-2): 137-149, 2001) (Year: 2001).*
Lin et al. (African Journal of Biotechnology, 10(79):18294-18302, 2011) (Year: 2011).*
Chu et al (An Update on Anti-CD137 Antibodies in Immunotherapies for Cancer. Int J Mol Sci. Apr. 12, 2019;20(8):1822. doi: 10.3390/ijms20081822.) (Year: 2019).*
International Search Report on PCT/US2020/12080.
Supplementary Partial European Search Report on EP20736004.
Supplementary European Search Report on EP20736004.
First Office Action notice of JP2 021-538846 application.

* cited by examiner

*Primary Examiner* — Elizabeth C. Kemmerer
*Assistant Examiner* — Ashley H. Gao
(74) *Attorney, Agent, or Firm* — Yong Chen; Lin Sun-Hoffman; Liu Chen & Hoffman LLP

(57) ABSTRACT

The present disclosure provides isolated binding molecules that bind to and activates CD137, vectors comprising a nucleic acid molecules encoding an amino acid sequence of the binding molecules, host cells containing the vectors, methods of making the binding molecules, pharmaceutical compositions containing the binding molecules, and methods of using such antibodies, antibody fragments and derivatives and polypeptides, including methods of treating a disease requiring stimulation of immune responses including cancer.

17 Claims, 5 Drawing Sheets
Specification includes a Sequence Listing.

CD137 AGONIST ANTIBODIES AND USES THEREOF

CROSS REFERENCE TO RELATED APPLICATION

This application claims priority to U.S. Provisional Application No. 62/787,509, filed Jan. 2, 2019, the disclosure of which is incorporated by reference herein in its entirety.

INCORPORATION OF SEQUENCE LISTING

This application includes a Sequence Listing which is being submitted in ASCII format via EFS-Web, named "QLSF001PCT_ST25.txt," which is 73.8 KB in size and created on Jan. 2, 2020. The contents of the Sequence Listing are incorporated herein by reference in their entirety.

BACKGROUND OF THE INVENTION

CD137 is a member of the Tumor Necrosis Factor (TNF) receptor family. Its alternative names are Tumor Necrosis Factor Receptor Superfamily member 9 (TNFRSF9), 4-1BB and Receptor Induced by Lymphocyte Activation (ILA). CD137 can be expressed by activated T cells, but to a larger extent on CD8 than on CD4 T cells. In addition, the CD137 expression is found on dendritic cells, follicular dendritic cells, natural killer cells, granulocytes and cells of blood vessel walls at sites of inflammation. One characteristic activity of CD137 is its costimulatory activity for activated T cells. Crosslinking of CD137 enhances T cell proliferation, IL-2 secretion survival and cytolytic activity. Further, it can enhance immune activity to eliminate tumors in mice.

CD137 can be induced on TCR activation as a T-cell costimulatory receptor (Nam et al., *Curr. Cancer Drug Targets*, 5:357-363 (2005); Watts et al., *Annu. Rev. Immunol.*, 23:23-68 (2005)). In addition to its expression on activated CD4+ and CD8+ T cells, CD137 is also expressed on CD4+CD25+ regulatory T cells. Its natural ligand, CD137L, has been described on antigen-presenting cells including B cells, monocyte/macrophages, and dendritic cells (Watts et al., *Annu. Rev. Immunol.*, 23:23-68 (2005)).

Signaling through CD137 by either CD137L or agonistic monoclonal antibodies (mAbs) binding CD137 leads to increased TCR-induced T cell proliferation, cytokine production and functional maturation, and prolonged CD8+ T cell survival. These effects result from: (1) the activation of the NF-KB, c-Jun NH2-terminal kinase/stress-activated protein kinase (JNK/SAPK), and p38 mitogen-activated protein kinase (MAPK) signaling pathways, and (2) the control of anti-apoptotic and cell cycle-related gene expression. Experiments performed in both CD137 and CD137L-deficient mice have additionally demonstrated the importance of CD137 costimulation in the generation of a fully competent T cell response.

IL-2 and IL-15 activated NK cells express CD137, and ligation of CD137 by agonistic mAbs stimulates NK cell proliferation and IFN-γ secretion, but not their cytolytic activity. Furthermore, CD137-stimulated NK cells promote the expansion of activated T cells in vitro. In accordance with their costimulatory function, agonist mAbs against CD137 have been shown to promote rejection of cardiac and skin allografts, eradicate established tumors, broaden primary antiviral CD8+ T cell responses, and increase T cell cytolytic potential. These studies support the view that CD137 signaling promotes T cell function which may enhance immunity against tumors and infection.

Anti-CD137 antibodies have been disclosed in U.S. 2005/0095244, issued U.S. Pat. No. 7,288,638 (such as 20H4.9-IgG4 [1007 or BMS-663513] or 20H4.9-IgG1 [BMS-663031]); U.S. Pat. No. 6,887,673 [cxE9 or BMS-554271]; U.S. Pat. Nos. 7,214,493; 6,303,121; 6,569,997; 6,905,685; 6,355,476; 6,362,325 [IDS or BMS-469492; 3H3 or BMS-469497; or 3E1]; U.S. Pat. No. 6,974,863 (such as 53A2); or U.S. Pat. No. 6,210,669 (such as IDS, 3B8, or 3E1), or U.S. Pat. No. 8,337,850. Additional CD137 agonistic antibodies are described in U.S. 2016/0244528, U.S. Pat. Nos. 5,928,893; 6,303,121, 6,569,997, and 8,137,667.

SUMMARY OF THE INVENTION

The present disclosure provides isolated monoclonal anti-CD137 agonist antibodies, and antigen-binding portions thereof that specifically bind to human CD137.

In an aspect of the invention, an isolated monoclonal anti-CD137 agonist antibody, or antigen-binding portion thereof comprises a heavy chain variable region CDR3 comprising SEQ ID NO:8. In some embodiments, the monoclonal anti-CD137 agonist antibody, or antigen-binding portion thereof further comprises a heavy chain variable region CDR1 comprising SEQ ID NO:6 and a heavy chain variable region CDR2 comprising SEQ ID NO:7. In preferred embodiments, the monoclonal anti-CD137 agonist antibody, or antigen-binding portion thereof further comprises: (a) a light chain variable region CDR1 comprising SEQ ID NO:3; (b) a light chain variable region CDR2 comprising SEQ ID NO:4; and (c) a light chain variable region CDR3 comprising SEQ ID NO:5. In one embodiment, the antibody or portion comprises a light chain variable region amino acid sequence having at least 95% identity to SEQ ID NO:1 and a heavy chain variable region amino acid sequence having at least 95% identity to SEQ ID NO:2. In another embodiment, the antibody or portion comprises a heavy chain variable region comprising an amino acid sequence that has at least 95%, at least 96%, at least 97%, at least 98%, or at least 99% identical to a sequence as set forth in SEQ ID NO:2.

In an aspect of the invention, an isolated monoclonal anti-CD137 agonist antibody, or antigen-binding portion thereof comprises a heavy chain variable region CDR3 comprising SEQ ID NO:31. In some embodiments, the monoclonal anti-CD137 agonist antibody, or antigen-binding portion thereof further comprises a heavy chain variable region CDR1 comprising SEQ ID NO:29 and a heavy chain variable region CDR2 comprising SEQ ID NO:30. In preferred embodiments, the monoclonal anti-CD137 agonist antibody, or antigen-binding portion thereof further comprises: (a) a light chain variable region CDR1 comprising SEQ ID NO:26; (b) a light chain variable region CDR2 comprising SEQ ID NO:27; and (c) a light chain variable region CDR3 comprising SEQ ID NO:28. In one embodiment, the antibody or portion comprises a light chain variable region amino acid sequence having at least 95% identity to SEQ ID NO:35 and a heavy chain variable region amino acid sequence having at least 95% identity to SEQ ID NO:36. In another embodiment, the antibody or portion comprises a heavy chain variable region comprising an amino acid sequence that is at least 95%, at least 96%, at least 97%, at least 98%, or at least 99% identical to a sequence as set forth in SEQ ID NO:36.

In another aspect of the invention, an isolated monoclonal anti-CD137 agonist antibody or an antigen-binding portion thereof comprises a heavy chain variable region comprising an amino sequence selected from the group consisting of SEQ ID NOs:22-25 and a light chain variable region comprising an amino sequence selected from the group consisting of SEQ ID NOs:18-21.

In another aspect of the invention, an isolated monoclonal anti-CD137 agonist antibody or an antigen-binding portion thereof comprises: a heavy chain variable region comprising an amino sequence selected from the group consisting of SEQ ID NOs: 13-17 and a light chain variable region comprising an amino sequence selected from the group consisting of SEQ ID NOs:9-12.

The antibodies of the disclosed invention can be further engineered into formats suitable for human therapeutics by modifications that minimize immunogenicity. Suitable antibodies include, but are not limited to chimeric antibodies and humanized antibodies. The affinity, stability and specificity of the disclosed antibodies can also be further optimized by techniques known to one of skill in the art. Other formats can involve oligomerization, drug conjugation and fusion of the disclosed antibodies with other functional proteins.

The antibodies of the disclosed invention can be, for example, full-length antibodies, for example of an IgG1, IgG2, IgG3, or IgG4 isotype. Alternatively, the disclosed antibodies can be antibody fragments, such as Fab, Fab' and F(ab')$_2$ fragments, diabody, triabody, tetrabody, single-chain variable region fragment (scFv), disulfide-stabilized variable region fragment (dsFv), and half antibodies. Alternatively, the disclosed antibodies can be bispecific antibodies.

In another aspect of the invention, an isolated monoclonal antibody or antigen binding portion thereof comprises a light chain comprises an amino acid sequence selected from the group consisting of SEQ ID NOs:33, 37-39 and a heavy chain comprising an amino acid sequence selected from the group consisting of SEQ ID NOs:32, 34, 40-42.

In another aspect of the invention, an isolated monoclonal antibody or antigen binding portion thereof comprises a light chain comprising an amino acid sequence selected from the group consisting of SEQ ID NOs:43-46 and a heavy chain comprising an amino acid sequence selected from the group consisting of SEQ ID NOs:47-50.

In some embodiments, the anti-CD137 agonist antibody, or antigen-binding portion thereof binds to and activates human CD137. Therefore the antibody, or antigen-binding portion can stimulate an anti-tumor immune response. In some embodiments, the anti-CD137 agonist antibody, or antigen-binding portion thereof binds to and activates non-human primate CD137. In some embodiments, the anti-CD137 agonist antibody, or antigen-binding portion thereof binds to and activates mammalian CD137.

In another aspect of the invention, a composition comprising the isolated anti-CD137 agonist monoclonal antibody, or antigen-binding portion thereof is also provided.

In another aspect of the invention, a pharmaceutical composition comprising the isolated anti-CD137 agonist monoclonal antibody, or antigen-binding portion thereof and a pharmaceutically acceptable carrier are also provided. Compositions comprising an immunoconjugate of the invention and a pharmaceutically acceptable carrier are also provided.

In another aspect of the invention, a vector comprising an isolated nucleic acid molecule encoding the antibody, or antigen-binding portion thereof, and a host cell comprising an expression vector comprising said nucleic acid molecule are also provided.

The present invention further provides a method of stimulating immune responses using the anti-CD137 agonist antibodies of the disclosed invention. For example, in one embodiment, the disclosed invention provides a method for treating a subject in need thereof, comprising the step of administering to the subject an effective amount of the antibody or antigen-binding portion of the disclosed invention.

In another aspect, the disclosed invention provides a method for treating cancer in a human comprising the step of administering to the human the anti-CD137 agonist antibody or antigen-binding portion of the disclosed invention in an amount effective to treat said cancer.

In another aspect, the disclosed invention provides a method for treating infectious diseases in a human comprising the step of administering to the human the anti-CD137 agonist antibody or antigen-binding portion of the disclosed invention in an amount effective to treat said infectious diseases.

Other features and advantages of the instant disclosure will be apparent from the following detailed description and examples, which should not be construed as limiting. The contents of all references, GenBank entries, patents and published patent applications cited throughout this application are expressly incorporated herein by reference.

BRIEF DESCRIPTION OF THE DRAWINGS

Exemplary embodiments are illustrated in referenced figures. It is intended that the embodiments and figures disclosed herein are to be considered illustrative rather than restrictive.

DETAILED DESCRIPTION OF THE INVENTION

Figure 1A:
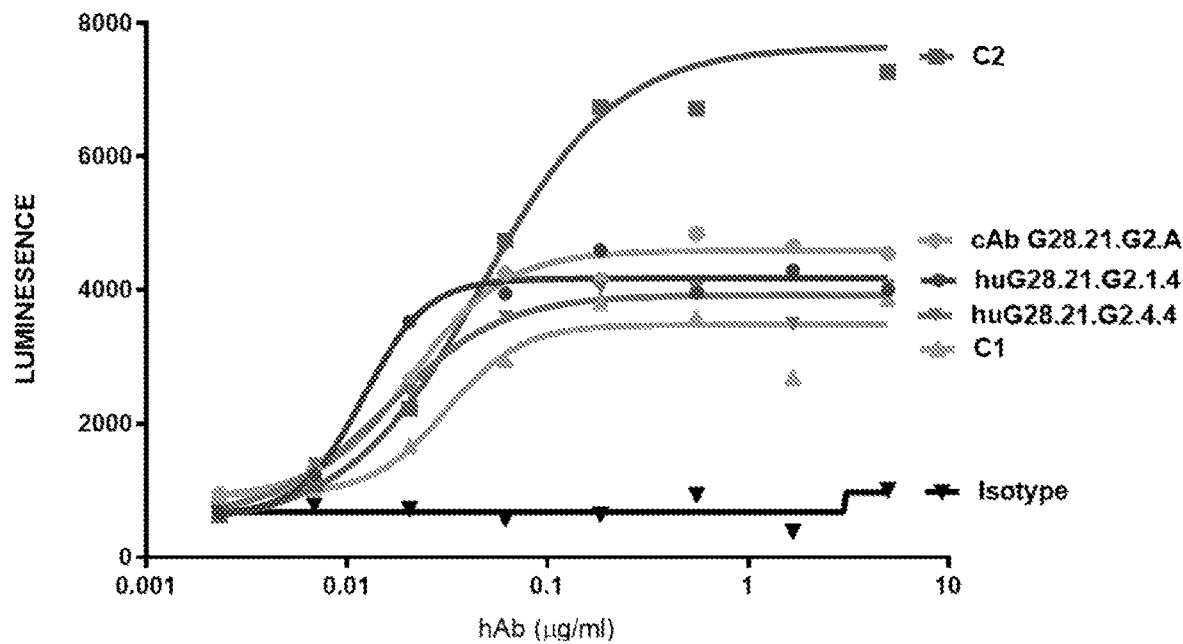
FIGS. 1A and 1B show anti-4-1BB (anti-CD137) agonist antibody of the present disclosure induces NF-KB reporter activation.

The following embodiments and aspects thereof are described and illustrated in conjunction with systems, compositions and methods which are meant to be exemplary and illustrative, not limiting in scope.

Definitions

As used herein the term "comprising" or "comprises" is used in reference to compositions, methods, and respective component(s) thereof, that are useful to an embodiment, yet open to the inclusion of unspecified elements, whether useful or not. It will be understood by those within the art that, in general, terms used herein are generally intended as "open" terms (e.g., the term "including" should be interpreted as "including but not limited to," the term "having" should be interpreted as "having at least," the term "includes" should be interpreted as "includes but is not limited to," etc.).

Unless stated otherwise, the terms "a" and "an" and "the" and similar references used in the context of describing a particular embodiment of the application (especially in the context of claims) can be construed to cover both the singular and the plural. The recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (for example, "such as") provided with respect to certain embodiments herein is intended merely to better illuminate the application and does not pose a limitation on the scope of the application otherwise claimed. The abbreviation, "e.g." is derived from the Latin exempli gratia, and is used herein to indicate a non-limiting example. Thus, the abbreviation "e.g." is synonymous with the term "for example." No language in the specification should be construed as indicating any non-claimed element essential to the practice of the application.

As used herein, the term "about" refers to a measurable value such as an amount, a time duration, and the like, and encompasses variations of ±20%, ±10%, ±5%, ±1%, ±0.5% or ±0.1% from the specified value.

The term "epitope" as used herein can include any protein determinant capable of specific binding to an immunoglobulin or T-cell receptor. Epitopic determinants usually consist of chemically active surface groupings of molecules such as amino acids or sugar side chains and usually have specific three-dimensional structural characteristics, as well as specific charge characteristics. An antibody is said to specifically bind an antigen when the equilibrium dissociation constant is ≤1 µM, preferably ≤100 nM and most preferably ≤10 nM.

The term "$K_D$" can refer to the equilibrium dissociation constant of a particular antibody-antigen interaction.

The term "immune response" as used herein can refer to the action of, for example, lymphocytes, antigen presenting cells, phagocytic cells, granulocytes, and soluble macromolecules produced by the above cells or the liver (including antibodies, cytokines, and complement) that results in selective damage to, destruction of, or elimination from an organism of invading pathogens, cells or tissues infected with pathogens, cancerous cells, or, in cases of autoimmunity or pathological inflammation, normal organismal cells or tissues.

An "antigen-specific T cell response" as used herein can refer to responses by a T cell that result from stimulation of the T cell with the antigen for which the T cell is specific. Non-limiting examples of responses by a T cell upon antigen-specific stimulation include proliferation and cytokine production (e.g., IL-2 production).

As used herein, the term "antibody" refers to an intact immunoglobulin or to a monoclonal or polyclonal antigen-binding fragment with the Fc (crystallizable fragment) region or FcRn binding fragment of the Fc region, referred to herein as the "Fc fragment" or "Fc region". Antigen-binding fragments may be produced by recombinant DNA techniques or by enzymatic or chemical cleavage of intact antibodies. Antigen-binding fragments include, inter alia, Fab, Fab', F(ab')2, Fv, dAb, and complementarity determining region (CDR) fragments, single-chain antibodies (scFv), single region antibodies, chimeric antibodies, diabodies and polypeptides that contain at least a portion of an immunoglobulin that is sufficient to confer specific antigen binding to the polypeptide. The Fc region includes portions of two heavy chains contributing to two or three classes of the antibody. The Fc region may be produced by recombinant DNA techniques or by enzymatic (e.g. papain cleavage) or via chemical cleavage of intact antibodies.

The term "antibody fragment," as used herein, refers to a protein fragment that comprises only a portion of an intact antibody, generally including an antigen binding site of the intact antibody and thus retaining the ability to bind antigen. Examples of antibody fragments encompassed by the present definition include: (i) the Fab fragment, having VL, CL, VH and CH1 regions; (ii) the Fab' fragment, which is a Fab fragment having one or more cysteine residues at the C-terminus of the CH1 region; (iii) the Fd fragment having VH and CH1 regions; (iv) the Fd' fragment having VH and CH1 regions and one or more cysteine residues at the C-terminus of the CH1 region; (v) the Fv fragment having the VL and VH regions of a single arm of an antibody; (vi) the dAb fragment (Ward et al., Nature 341, 544-546 (1989)) which consists of a VH region; (vii) isolated CDR regions; (viii) F(ab')2 fragments, a bivalent fragment including two Fab' fragments linked by a disulfide bridge at the hinge region; (ix) single chain antibody molecules (e.g., single chain Fv; scFv) (Bird et al., Science 242:423-426 (1988); and Huston et al., PNAS (USA) 85:5879-5883 (1988)); (x) "diabodies" with two antigen binding sites, comprising a heavy chain variable region (VH) connected to a light chain variable region (VL) in the same polypeptide chain (see, e.g., EP 404,097; WO 93/11161; and Hollinger et al., Proc. Natl. Acad. Sci. USA, 90:6444-6448 (1993)); (xi) "linear antibodies" comprising a pair of tandem Fd segments (VH-CH1-VH-CH1) which, together with complementary light chain polypeptides, form a pair of antigen binding regions (Zapata et al. Protein Eng. 8(10):1057-1062 (1995); and U.S. Pat. No. 5,641,870).

"Single-chain variable fragment", "single-chain antibody variable fragments" or "scFv" antibodies as used herein refers to forms of antibodies comprising the variable regions of only the heavy (VH) and light (VL) chains, connected by a linker peptide. The scFvs are capable of being expressed as a single chain polypeptide. The scFvs retain the specificity of the intact antibody from which it is derived. The light and heavy chains may be in any order, for example, VH-linker-VL or VL-linker-VH, so long as the specificity of the scFv to the target antigen is retained.

An "isolated antibody", as used herein, can refer to an antibody that is substantially free of other antibodies having different antigenic specificities (e.g., an isolated antibody that specifically binds a CD137 protein can be substantially free of antibodies that specifically bind antigens other than CD137 proteins). An isolated antibody that specifically binds a human CD137 protein can, however, have cross-reactivity to other antigens, such as CD137 proteins from other species. Moreover, an isolated antibody can be substantially free of other cellular material and/or chemicals.

Anti-CD137 agonist antibody-producing cells, e.g., hybridomas, can be selected, cloned and further screened for desirable characteristics, including robust growth, high antibody production and desirable antibody characteristics. Hybridomas can be expanded in vivo in syngeneic animals, in animals that lack an immune system, e.g., nude mice, or in cell culture in vitro. Methods of selecting, cloning and expanding hybridomas are well known to those of ordinary skill in the art.

The terms "monoclonal antibody" or "monoclonal antibody composition" as used herein can refer to a preparation of antibody molecules of single molecular composition. A monoclonal antibody composition displays a single binding specificity and affinity for a particular epitope.

The term "recombinant human antibody", as used herein, can refer to all human antibodies that are prepared, expressed, created or isolated by recombinant means, such as (a) antibodies isolated from an animal (e.g., a mouse) that is transgenic or transchromosomal for human immunoglobulin genes or a hybridoma prepared therefrom (described below), (b) antibodies isolated from a host cell transformed to express the human antibody, e.g., from a transfectoma, (c) antibodies isolated from a recombinant, combinatorial human antibody library, and (d) antibodies prepared, expressed, created or isolated by any other means that involve splicing of human immunoglobulin gene sequences to other DNA sequences. Such recombinant human antibodies have variable regions in which the framework and CDR regions are derived from human germline immunoglobulin sequences. In certain embodiments, however, such recombinant human antibodies can be subjected to in vitro mutagenesis (or, when an animal transgenic for human Ig sequences is used, in vivo somatic mutagenesis) and thus the amino acid sequences of the VH and VL regions of the recombinant antibodies are sequences that, while derived from and related to human germline VH and VL sequences, may not naturally exist within the human antibody germline repertoire in vivo.

The term "isotype" can refer to the antibody class (e.g., IgM or IgG1) that is encoded by the heavy chain constant region genes. An antibody can be an immunoglobulin G (IgG), an IgM, an IgE, an IgA or an IgD molecule, or is derived therefrom.

The phrases "an antibody recognizing an antigen" and "an antibody specific for an antigen" are used interchangeably herein with the term "an antibody which binds specifically to an antigen."

As used herein, an antibody that "specifically binds human CD137" can refer to an antibody that binds to a human CD137 protein (and possibly a CD137 protein from one or more non-human species) but does not substantially bind to non-CD137 proteins. Preferably, the antibody binds to a human CD137 protein with "high affinity," namely with a $K_D$ of $1\times10^{-7}$ M or less, more preferably $5\times10^{-8}$ M or less, more preferably $3\times10^{-8}$ M or less, more preferably $1\times10^{-8}$ M or less, more preferably $5\times10^{-9}$ M or less or even more preferably $1\times10^{-9}$ M or less.

The term "does not substantially bind" to a protein or cells, as used herein, can mean that it cannot bind or does not bind with a high affinity to the protein or cells, i.e., binds to the protein or cells with an $K_D$ of $2\times10^{-6}$ M or more, more preferably $1\times10^{-5}$ M or more, more preferably $1\times10^{-4}$ M or more, more preferably $1\times10^{-3}$ M or more, even more preferably $1\times10^{-2}$ M or more.

The term "high affinity" for an IgG antibody can refer to an antibody having a $K_D$ of $1\times10^{-6}$ M or less, preferably $1\times10^{-7}$ M or less, more preferably $1\times10^{-8}$ M or less, even more preferably $1\times10^{-9}$ M or less, even more preferably $1\times10^{-10}$ M or less for a target antigen. However, "high affinity" binding can vary for other antibody isotypes.

The term "pharmaceutical formulation" refers to a preparation which is in such form as to permit the biological activity of an active ingredient contained therein to be effective, and which contains no additional components which are unacceptably toxic to a subject to which the formulation would be administered.

A "therapeutically effective amount" of an agent, e.g., a pharmaceutical formulation or cells, refers to an amount effective, at dosages and for periods of time necessary, to achieve a desired therapeutic result, such as for treatment of a disease, condition, or disorder, and/or pharmacokinetic or pharmaco-dynamic effect of the treatment. The therapeutically effective amount may vary according to factors such as the disease state, age, sex, and weight of the subject, and the populations of cells administered. In some embodiments, the provided methods involve administering the cells and/or compositions at effective amounts, e.g., therapeutically effective amounts.

An "agonist antibody" as used herein, is an antibody that induces or increases the biological activity of an antigen (for example, CD137) to which the antibody binds. An agonist may, for example, facilitate a receptor's phosphorylation due to binding of the receptor to a ligand or may activate or grow cells activated by the receptor. In one embodiment, the antibodies of the invention are agonist anti-CD137 antibodies.

A "CDR grafted antibody" is an antibody comprising one or more CDRs derived from an antibody of a particular species or isotype and the framework of another antibody of the same or different species or isotype.

A "humanized antibody" has a sequence that differs from the sequence of an antibody derived from a non-human species by one or more amino acid substitutions, deletions, and/or additions, such that the humanized antibody is less likely to induce an immune response, and/or induces a less severe immune response, as compared to the non-human species antibody, when it is administered to a human subject. In one embodiment, certain amino acids in the framework and constant regions of the heavy and/or light chains of the non-human species antibody are mutated to produce the humanized antibody. In another embodiment, the constant region(s) from a human antibody are fused to the variable region(s) of a non-human species. In another embodiment, a humanized antibody is a CDR grafted antibody comprising one or more CDRs derived from an antibody of a particular species or isotype and the framework of human antibodies. In another embodiment, one or more amino acid residues in one or more CDR sequences of a non-human antibody are changed to reduce the likely immunogenicity of the non-human antibody when it is administered to a human subject, wherein the changed amino acid residues either are not critical for immunospecific binding of the antibody to its antigen, or the changes to the amino acid sequence that are made are conservative changes, such that the binding of the humanized antibody to the antigen is not significantly worse than the binding of the non-human antibody to the antigen. Examples of how to make humanized antibodies may be found in U.S. Pat. Nos. 6,054,297, 5,886,152 and 5,877,293.

The term "chimeric antibody" refers to an antibody that contains one or more regions from one antibody and one or more regions from one or more other antibodies. In one embodiment, one or more of the CDRs are derived from a human anti-CD137 antibody. In another embodiment, all of the CDRs are derived from a human anti-CD137 antibody. In another embodiment, the CDRs from more than one human anti-CD137 antibodies are mixed and matched in a chimeric antibody. For instance, a chimeric antibody may comprise a CDR1 from the light chain of a first human anti-CD137 antibody, a CDR2 and a CDR3 from the light chain of a second human anti-CD137 antibody, and the CDRs from the heavy chain from a third anti-CD137 antibody. Other combinations are possible.

The term "subject" can refer to any human or non-human animal. The subject can be male or female and can be any suitable age, including infant, juvenile, adolescent, adult, and geriatric subjects. The term "nonhuman animal"

includes all vertebrates, e.g., mammals and non-mammals, such as nonhuman primates, sheep, dogs, cats, cows, horses, chickens, rabbits, mice, rats, amphibians, and reptiles, although mammals are preferred, such as non-human primates, sheep, dogs, cats, cows and horses.

The binding of an antibody of the disclosed invention to CD137 can be assessed using one or more techniques well established in the art. For example, in a preferred embodiment, an antibody can be tested by ELISA assays, for example using a recombinant CD137 protein. Still other suitable binding assays include but are not limited to a flow cytometry assay in which the antibody is reacted with a cell line that expresses human CD137, such as HEK293 cells that have been transfected to express CD137 (e.g., human CD137) on their cell surface. Additionally or alternatively, the binding of the antibody, including the binding kinetics (e.g., $K_D$ value) can be tested in BIAcore binding assays, Octet Red96 (Pall) and the like.

Preferably, an antibody of the disclosed invention binds to a human CD137 protein with a $K_D$ of $5\times10^{-8}$ M or less, binds to a human CD137 protein with a $K_D$ of $2\times10^{-8}$ M or less, binds to a human CD137 protein with a $K_D$ of $5\times10^{-9}$ M or less, binds to a human CD137 protein with a $K_D$ of $4\times10^{-9}$ M or less, binds to a human CD137 protein with a $K_D$ of $3\times10^{-9}$ M or less, binds to a human CD137 protein with a $K_D$ of $2\times10^{-9}$ M or less, binds to a human CD137 protein with a $K_D$ of $1\times10^{-9}$ M or less.

The present disclosure relates to isolated monoclonal antibodies, or antigen binding portions thereof, which binds to and activates CD137, and uses thereof. In certain embodiments, the antibodies of the disclosed invention are derived from identified heavy and light chain germline sequences and/or comprise identified structural features such as CDR regions comprising identified amino acid sequences. This disclosure provides isolated antibodies, methods of making such antibodies and antigen-binding portions thereof of the disclosed invention. This disclosure also relates to methods of using the antibodies, such as using the anti-CD137 agonist antibodies of the disclosed invention to stimulate immune responses, alone or in combination with other immunostimulatory antibodies. Accordingly, also provided are methods of using the anti-CD137 agonist antibodies of the disclosed invention for example, including but not limited to, treating cancer in a human. Various aspects of the invention relate to antibodies and antibody fragments, pharmaceutical compositions, nucleic acids, recombinant expression vectors, and host cells for making such antibodies and fragments. Methods of using the antibodies of the invention to detect human CD137, to stimulate CD137 activity, either in vitro or in vivo, and to prevent or treat disorders such as cancer are also encompassed by the invention.

Complementarity determining regions (CDRs) are known as hypervariable regions both in the light chain and the heavy chain variable regions. The more highly conserved portions of variable regions are called the framework (FR). Complementarity determining regions (CDRs) and framework regions (FR) of a given antibody may be identified using the system described by Kabat et al. supra; Lefranc et al., supra and/or Honegger and Pluckthun, supra. Also familiar to those in the art is the numbering system described in Kabat et al. (1991, NIH Publication 91-3242, National Technical Information Service, Springfield, Va.). In this regard Kabat et al. defined a numbering system for variable region sequences that is applicable to any antibody. One of ordinary skill in the art can unambiguously assign this system of "Kabat numbering" to any variable region amino acid sequence, without reliance on any experimental data beyond the sequence itself.

In certain embodiments, the present invention provides anti-CD137 agonist antibodies or antigen-binding portions thereof. In one embodiment, the antibody or portion comprises (a) a light chain variable region CDR1 comprising SEQ ID NO:3; (b) a light chain variable region CDR2 comprising SEQ ID NO:4; (c) a light chain variable region CDR3 comprising SEQ ID NO:5; (d) a heavy chain variable region CDR1 comprising SEQ ID NO:6; (e) a heavy chain variable region CDR2 comprising SEQ ID NO:7; (f) a heavy chain variable region CDR3 comprising SEQ ID NO:8. In another embodiment, the antibody or portion comprises (a) a light chain variable region CDR1 comprising SEQ ID NO:26; (b) a light chain variable region CDR2 comprising SEQ ID NO:27; (c) a light chain variable region CDR3 comprising SEQ ID NO:28; (d) a heavy chain variable region CDR1 comprising SEQ ID NO:29; (e) a heavy chain variable region CDR2 comprising SEQ ID NO:30; (f) a heavy chain variable region CDR3 comprising SEQ ID NO:31.

In one embodiment, the present disclosure provides a monoclonal antibody or antigen-binding portion thereof that binds to a CD137 epitope, that comprises a light chain variable region amino acid sequence having at least 95% identity to SEQ ID NO:1 or 35 and a heavy chain variable region amino acid sequence having at least 95% identity to SEQ ID NO:2 or 36.

Given that each of these antibody Fab can bind to human CD137, the VH and VL sequences can be "mixed and matched" to create other anti-CD137 binding molecules of the invention. Preferably, when VH and VL chains are mixed and matched, a VH sequence from a particular VH/VL pairing is replaced with a structurally similar VH sequence. Likewise, preferably a VL sequence from a particular VH/VL pairing is replaced with a structurally similar VL sequence.

In some embodiments, the humanized antibody or antigen binding portion thereof comprises a heavy chain variable region comprising an amino acid sequence selected from the group consisting of SEQ ID NOs: 13-17 and a light chain variable region comprising an amino acid sequence selected from the group consisting of SEQ ID NOs: 9-12. Preferred heavy and light chain combinations include but not limited to:
- (a) a heavy chain variable region comprising the amino acid sequence of SEQ ID NO:13 and a light chain variable region comprising the amino acid sequence of SEQ ID NO:9;
- (b) a heavy chain variable region comprising the amino acid sequence of SEQ ID NO:14 and a light chain variable region comprising the amino acid sequence of SEQ ID NO:10;
- (c) a heavy chain variable region comprising the amino acid sequence of SEQ ID NO:15 and a light chain variable region comprising the amino acid sequence of SEQ ID NO:11;
- (d) a heavy chain variable region comprising the amino acid sequence of SEQ ID NO:16 and a light chain variable region comprising the amino acid sequence of SEQ ID NO:12;

In some embodiments, the humanized antibody or antigen binding portion thereof comprises a heavy chain variable region comprising an amino acid sequence selected from the group consisting of SEQ ID NOs:22-25 and a light chain variable region comprising an amino acid sequence selected from the group consisting of SEQ ID NOs:18-21. Preferred heavy and light chain combinations include but not limited to:
(a) a heavy chain variable region comprising the amino acid sequence of SEQ ID NO:22 and a light chain variable region comprising the amino acid sequence of SEQ ID NO:18;
(b) a heavy chain variable region comprising the amino acid sequence of SEQ ID NO:23 and a light chain variable region comprising the amino acid sequence of SEQ ID NO:19;
(c) a heavy chain variable region comprising the amino acid sequence of SEQ ID NO:24 and a light chain variable region comprising the amino acid sequence of SEQ ID NO:20;
(d) a heavy chain variable region comprising the amino acid sequence of SEQ ID NO:25 and a light chain variable region comprising the amino acid sequence of SEQ ID NO:21;

In some embodiments, the humanized anti-CD137 agonist antibody or antigen binding portion thereof comprises a light chain comprising an amino acid sequence selected from the group consisting of SEQ ID NOs:33, 37-39 and a heavy chain comprising an amino acid sequence selected from the group consisting of SEQ ID NOs:32, 34, and 40-42.

In some embodiments, the humanized anti-CD137 agonist antibody or antigen binding portion thereof comprises a light chain comprising an amino acid sequence selected from the group consisting of SEQ ID NOs:43-46 and a heavy chain comprising an amino acid sequence selected from the group consisting of SEQ ID NOs:47-50.

In some embodiments, the invention provides an anti-CD137 antibody, or an antigen-binding fragment thereof, comprising a heavy chain comprising a CDR3 region as set forth in any one of SEQ ID NOs:8 and 31, and comprising a heavy chain variable region comprising an amino acid sequence that has at least 95%, at least 96%, at least 97%, at least 98%, or at least 99% identical to a sequence as set forth in any one of SEQ ID NOs:2, 13-17, 22-25, and 36.

In some embodiments, the invention provides an anti-CD137 antibody, or an antigen-binding fragment thereof, comprising a light chain comprising a CDR3 region as set forth in any one of SEQ ID NOs:5 and 28, and having a light chain variable region comprising an amino acid sequence that has at least 95%, at least 96%, at least 97%, at least 98%, or at least 99% identical to a sequence as set forth in any one of SEQ ID NOs:1, 9-12, 18-21, and 35.

Thus, in certain embodiments, the CDR3 region is held constant, while variability may be introduced into the remaining CDRs and/or framework regions of the heavy and/or light chains, while the antibody, or antigen binding fragment thereof, retains the ability to bind to CD137 and retains the functional characteristics, e.g., binding affinity, of the parent.

In some embodiments, the substitutions made within a heavy or light chain that is at least 95% identical (or at least 96% identical, or at least 97% identical, or at least 98% identical, or at least 99% identical) are conservative amino acid substitutions. A "conservative amino acid substitution" is one in which an amino acid residue is substituted by another amino acid residue having a side chain (R group) with similar chemical properties (e.g., charge or hydrophobicity). In general, a conservative amino acid substitution will not substantially change the functional properties of a protein. In cases where two or more amino acid sequences differ from each other by conservative substitutions, the percent sequence identity or degree of similarity may be adjusted upwards to correct for the conservative nature of the substitution. Means for making this adjustment are well-known to those of skill in the art. See, e.g., Pearson (1994) Methods Mol. Biol. 24: 307-331, herein incorporated by reference. Examples of groups of amino acids that have side chains with similar chemical properties include (1) aliphatic side chains: glycine, alanine, valine, leucine and isoleucine; (2) aliphatic-hydroxyl side chains: serine and threonine; (3) amide-containing side chains: asparagine and glutamine; (4) aromatic side chains: phenylalanine, tyrosine, and tryptophan; (5) basic side chains: lysine, arginine, and histidine; (6) acidic side chains: aspartate and glutamate, and (7) sulfur-containing side chains are cysteine and methionine.

The present disclosure also provides isolated polynucleotides (or nucleic acid molecules) encoding the various amino acid sequences (e.g., those of the antibodies or antigen-binding portion(s) thereof) disclosed herein, vectors containing the polynucleotides, cells (or host cells) containing the vectors, cells containing or expressing the various amino acid sequences disclosed herein, methods of making the antibodies (and/or fragments thereof), pharmaceutical compositions containing the antibodies disclosed herein, etc.

Unless stated otherwise, or implicit from context, the following terms and phrases include the meanings provided below. Unless explicitly stated otherwise, or apparent from context, the terms and phrases below do not exclude the meaning that the term or phrase has acquired in the art to which it pertains. The definitions are provided to aid in describing particular embodiments, and are not intended to limit the claimed invention, because the scope of the invention is limited only by the claims. Unless otherwise defined, all technical and scientific terms used herein have the same meaning as commonly understood by one of ordinary skill in the art to which this invention belongs.

All publications herein are incorporated by reference to the same extent as if each individual publication or patent application was specifically and individually indicated to be incorporated by reference. The following description includes information that may be useful in understanding the present invention. It is not an admission that any of the information provided herein is prior art or relevant to the presently claimed invention, or that any publication specifically or implicitly referenced is prior art.

WORKING EXAMPLES

The following examples are not intended to limit the scope of the claims to the invention, but is rather intended to be exemplary of certain embodiments. Any variations in the exemplified methods which occur to the skilled artisan are intended to fall within the scope of the present invention.

Vector Construction:

Vector pcDNA3.4TOPO (Invitrogen) was ligated to a short polylinker containing EcoRI, XhoI, and NotI. The resulting plasmid was digested with EcoRI and NotI restriction enzymes and purified by gel electrophoresis. For heavy chain cloning, the prepared vector was assembled using Gibson assembly the prepared vector, a gblock encoding and VH region (IDT), and human IgG2 gblock encoding an XhoI site at the junction of the J-chain and CH1 region. The plasmid was prepared and digested with EcoRI and XhoI to accommodate all the humanized variable heavy (VH) regions with an IgG2 isotype. All assembly was done with the Gibson method (NEB). Variable light regions were constructed with a similar method using gblocks to assemble Vkappa regions with a gblock fragment which encoded the constant kappa (Ck).

Protein Expression:

Plasmids were prepped and transfected into Expi293 or ExpiCHO cells using the transient expression system (ThermoFisher). Briefly, plasmids were transfected into 3e6 cells/ml cells at 1 µg plasmid DNA total/ml culture. The heavy chain and light chain plasmids were mixed at a 1:1 ratio. Cultures were incubated at 37° C., shaking. After 16 hours, Transfection Enhancer 1 and 2 were added to the cultures and incubation was continued for six days. Supernatant was filtered, and protein titers were determined by an IgG quantitation protocol using the Octet Red96 (Pall). (Table 1) IgG was purified by Mab Select Sure Protein-A column purification on an ACTA PURE system and dialyzed overnight in PBS.

TABLE 1

Octet Data. Mono-valent Binding Kinetics of Anti-4-1BB Antibodies

| | Response | KD (M) | kon(1/Ms) | kdis(1/s) | $T_{1/2}$ Life (min) |
|---|---|---|---|---|---|
| C1 | 0.1222 | 4.15E−08 | 2.79E+05 | 1.16E−02 | 1.0 |
| C2 | 0.1436 | 3.51E−08 | 1.62E+05 | 5.69E−03 | 2.0 |
| cAb 137QL.F1.1.G2 | 0.1384 | 4.19E−08 | 1.38E+05 | 5.78E−03 | 2.0 |
| cAB 137QL.G28.21.G2 | 0.2045 | 1.40E−08 | 3.73E+05 | 5.23E−03 | 2.2 |
| huG28.21.G2.1.4 | 0.1811 | 1.53E−08 | 4.26E+05 | 6.52E−03 | 1.8 |
| huG28.21.G2.4.4 | 0.1747 | 1.04E−08 | 4.49E+05 | 4.67E−03 | 2.5 |
| huF1.1.G2.2.4 | 0.1197 | 4.06E−08 | 1.38E+05 | 5.59E−03 | 2.1 |
| huF1.1.G2.4.4 | 0.1369 | 4.04E−08 | 1.53E+05 | 6.18E−03 | 1.9 |

Flow Cytometry

Human/Cyno/Mouse 4-1BB transfected HEK293 cells or PHA-P stimulated PBMCs were incubated with serial diluted anti-4-1BB antibodies in FACS buffer (DPBS+ 2% FBS+ 0.05% sodium azide) followed by AF647-labeled F(ab')2 goat anti-human IgG and 7-AAD. In addition, PBMCs were incubated with FITC Mouse anti-human CD3. Stained 4-1BB expressing HEK293 samples were analyzed using FlowJo by gating on FSC/SSC, followed by live/dead cell gating, and human/Cynomolgous/Mouse 4-1BB+ cells (MFI Geo Mean denoted). Stained Lymphocyte samples were analyzed using FlowJo by gating on FSC/SSC, followed by live/dead cell gating, and CD3+ cells with 4-1BB positives. (Table 2 and Table 3)

TABLE 2

Flow cytometry and NK-kB luciferase detection. Anti-4-1BB mAbs bind to cell surface antigen. Anti-4-1BB mAbs do not bind to mouse 4-1BB or unstimulated human T Cells (data not shown). No NF-KB stimulation was observed in the absence of Fc cross-linking.

| | Cell Binding EC50 (µg/ml) | | | |
|---|---|---|---|---|
| | HEK293 cells over-expressing human 4-1BB | HEK293 cells over-expressing cyno 4-1BB | Activated T cells | NF-κB Stimulation (EC50 µg/ml) |
| F1.1 | 0.341 | 0.392 | 0.233 | 0.026 |
| G28.21 | 0.121 | 0.162 | 0.080 | 0.018 |
| C1 | 0.105 | 0.168 | 0.048 | 0.032 |

TABLE 3

Flow cytometry. Anti-4-1BB Antibodies bind to cell surface antigen.

| | HEK293 cells over-expressing human 4-1BB | HEK293 cells over-expressing cyno 4-1BB | Activated T cells |
|---|---|---|---|
| Chimeric F1.1 | 0.202 | 0.309 | |
| Chimeric G28.21 | 0.056 | 0.099 | |
| huF1.1.2.4 | 0.404 | 0.602 | 0.234 |
| huF1.1.4.4 | 0.379 | 0.545 | 0.146 |
| huG28.21.1.4 | 0.083 | 0.154 | 0.010 |
| huG28.21.4.4 | 0.086 | 0.135 | 0.010 |
| C1 | 0.053 | 0.091 | ~ to G28.21 |
| C2 | 0.051 | No Binding | 0.026 |

Figure 1B:
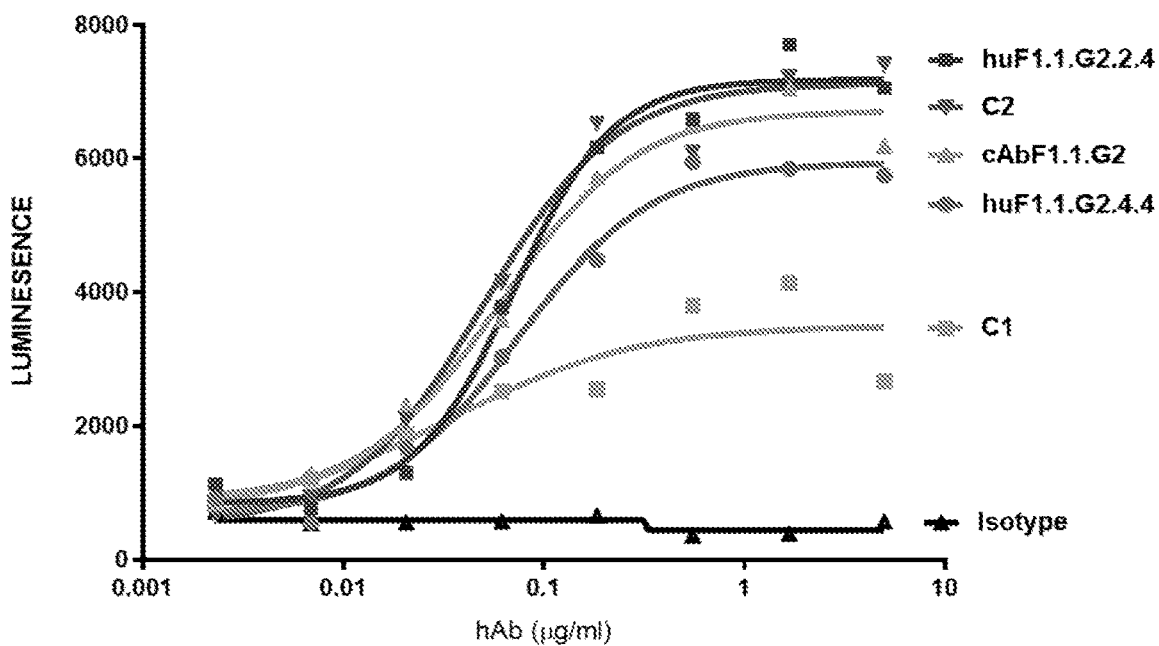

NF-κB Reporter Assay Using Human 4-1BB 293 Transfected Cells with Fc-Cross-Linking from CHOK1hFcgRIIA/CHOK1 Cells NF-κB Hu 4-1BB 293 transfected cells were made by transfecting HEK-Dual™ TNF-α cells (Invivogen) with 4-1BB and were used to measure TNF-α induced NF-kB activation. hFcgRIIA/CHOK1 transfected cells were used to provide cross-linking to anti-4-1BB IgGs. Cells were harvested with Accutase, washed, and resuspended with DMEM without phenol red+10% heat-inactivated Fetal Bovine Serum at $1 \times 10^6$ cells/ml. $5 \times 10^4$ NF-κB 4-1BB 293 transfected cells were co-cultured in Costar 3799 U-bottom 96-well plates with an equal number of hFcgRIIA/CHOK1 transfected cells or CHOK1 parental cells. Test antibodies, positive control antibodies (C1 & C2), and negative control (Isotype) were serially diluted in media and added to the cells. Following incubation at 37° C. for 18-22 hours, 20 µl of cell suspension was removed from the wells and mixed with 50 µl of luminescence assay reagent (Quanti-Luc, Invivo-Gen #rep-qlc) in an opaque 96 flat-bottom plate. Luminescence (RLUs) was measured on a Flexstation3 plate reader with integration of 100 ms. (FIGS. 1A and 1B) (Table 4).

TABLE 4

NF-KB reporter activation is induced by anti-4-1BB (anti-CD137) agonist antibody.

| | huF1.1.G2.2.4 | huF1.1.G2.4.4 | cAb F1.1.G2 | C2 | C1 |
|---|---|---|---|---|---|
| Bottom | 838 | 666 | 894 | 521 | 669 |
| Top | 7194 | 5942 | 6730 | 7140 | 3504 |
| HillSlope | 1.756 | 1.300 | 1.285 | 1.312 | 0.935 |
| EC50 | 0.071 | 0.074 | 0.060 | 0.050 | 0.033 |

TABLE 4-continued

| | huG28.21.G2.1.4 | huG28.21.G2.4.4 | cAb G28.21.G2 | C2 | C1 |
|---|---|---|---|---|---|
| Bottom | 625 | 592 | 879 | 492 | 933 |
| Top | 4173 | 3924 | 4592 | 7655 | 3482 |
| HillSlope | 2.715 | 1.546 | 1.845 | 1.290 | 2.336 |
| EC50 | 0.012 | 0.016 | 0.021 | 0.047 | 0.031 |

Figure 2A:
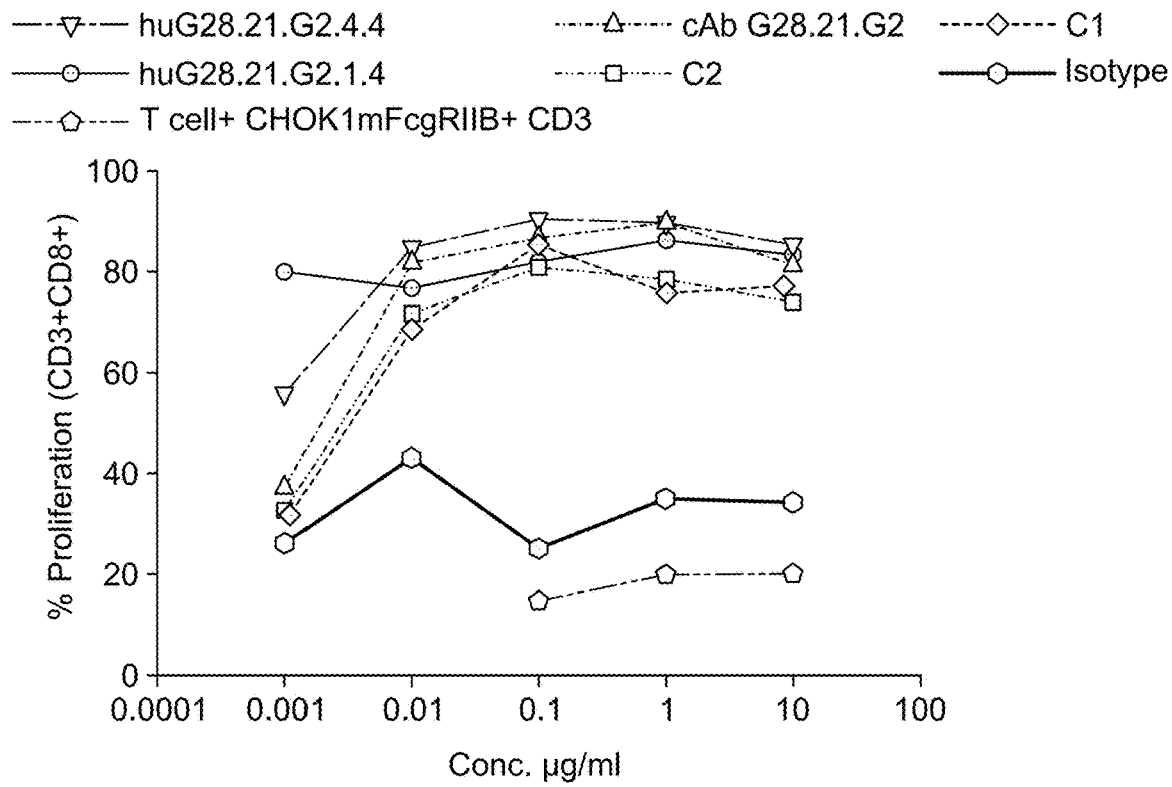
FIGS. 2A and 2B show anti-4-1BB (anti-CD137) agonist antibody of the present disclosure stimulates primary CD3+ CD8+ T cell proliferation.
Figure 2B:
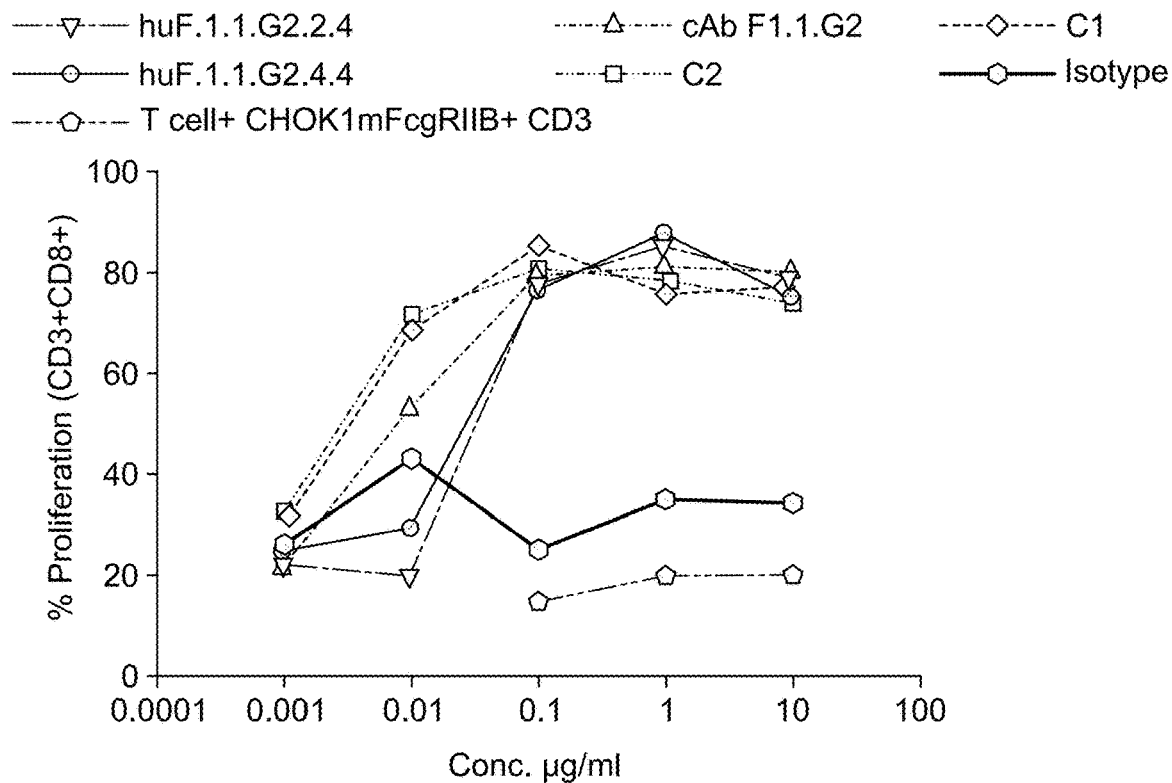
Figure 2C:
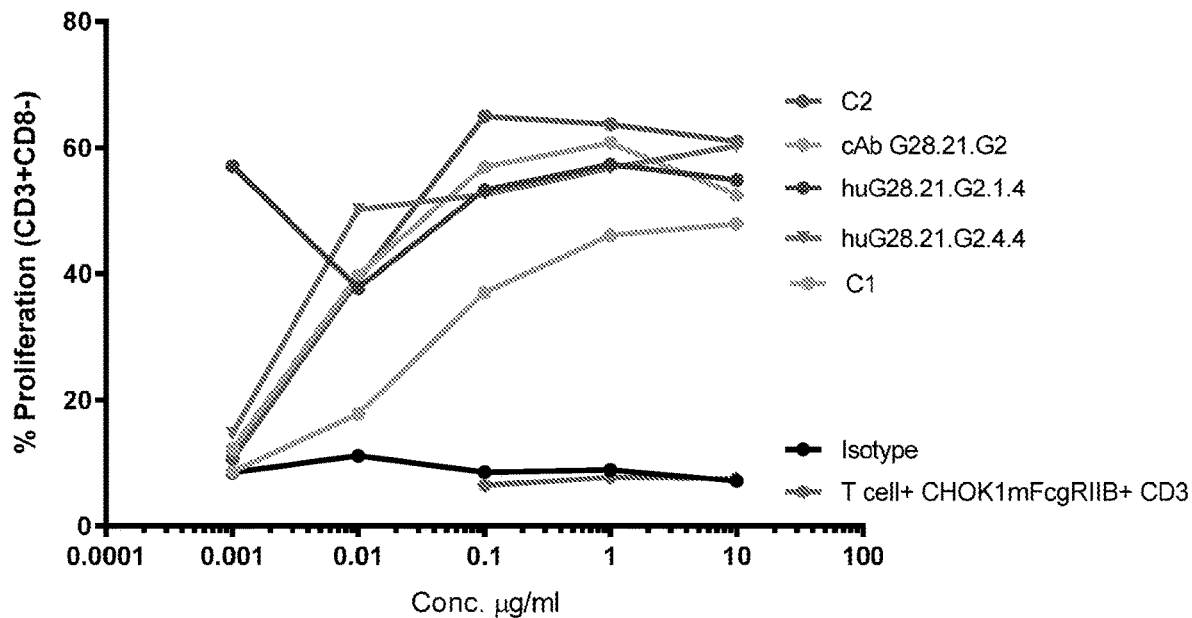
FIGS. 2C and 2D show anti-4-1BB (anti-CD137) agonist antibody stimulating primary CD3+CD8− T cell proliferation.
Figure 2D:
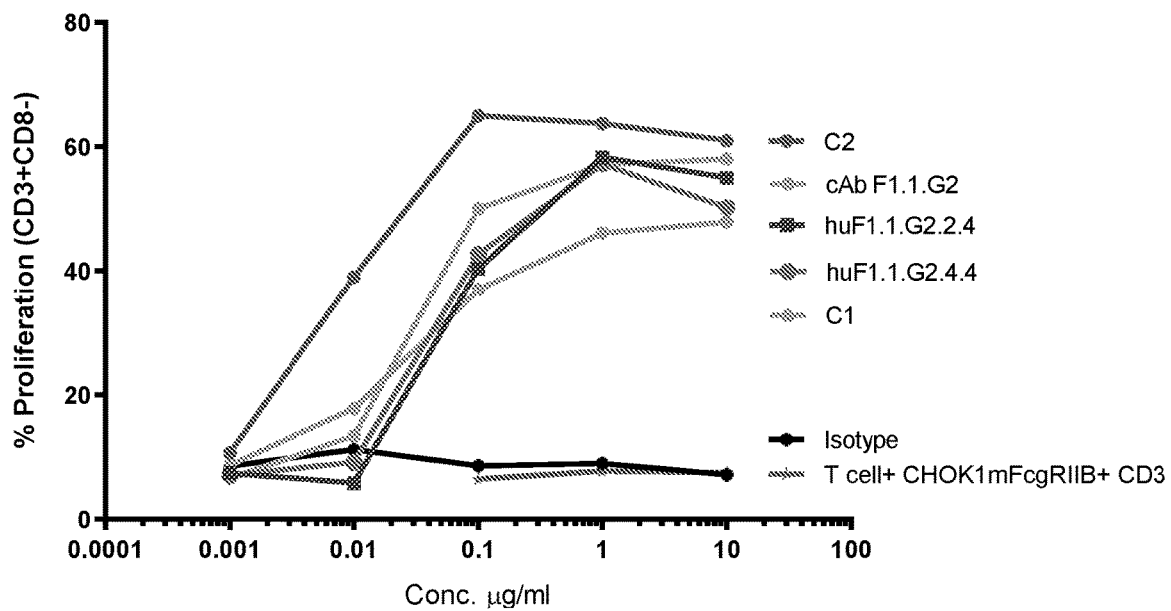

Anti-4-1BB Mediated T Cell Proliferation & Interferon Gamma Release Cross-Linked with CHOK1mFcgRIIB Transfected Cells T cells were prepared from Peripheral blood mononuclear cells (PBMCs) with the Pan T cell Isolation kit (Miltenyi Biotec product #130-096-535), resuspended in cold PBS, 0.5% bovine serum albumin (BSA) and 2 mM EDTA, pH 7.2, and labeled with Cell Trace Violet (ThermoFisher, cat #C34557) per kit instructions. Finally, labeled pan T cells were resuspended in Advanced RPMI-1640, 10% heat-inactivated FBS, 2-Mercaptoethanol (1:1000) at $2 \times 10^6$ cells/ml. CHOK1.mFcgRIIB-mCherry cells were cultured in F12 Ham, 10% FBS, 5 μg/ml Puromycin, harvested by Accutase, and resuspended in Advanced RPMI-1640, 10% heat-inactivated FBS, 2-Mercaptoethanol (1:1000) at $2 \times 10^5$ cells/ml. CHOK1 parental cells were prepared similarly without Puromycin in the media. To a 96-wells U-bottom culture plate, 100,000 labeled pan T cells/well were mixed with CHOK1mFcgRIIB-mCherry or CHOK1 at 10,000 cells/well, a 10:1 ratio. 10 ng/ml NA/LE Mouse anti-Human CD3 (clone UCHT-1) was added to all wells, and then serial diluted 4-1BB test antibodies, positive control antibody (C1 or C2), and negative control antibody (Isotype) at a starting concentration of 1 μg/ml were added. Control wells included CHOK1mFcgRIIB-mCherry, Pan T cells+CHOK1mFcgRIIB, Pan T cells+CHOK1mFcgRIIB+anti-human CD3, Pan T cells+anti-human CD3, and Pan T cells alone. Plates were incubated for 5 days in a 37° C. $CO_2$ incubator. Cells were further stained for flow cytometry with FITC anti-huCD3, PE anti-huCD8, and 7-AAD. Samples were analyzed using FlowJo by gating on FSC/SSC, followed by live/dead cell gating, then proliferation (CellTrace Violet) of CD3+/CD8+ T cells and CD3+/CD8− T cells. FIGS. 2A and 2B show anti-4-1BB (anti-CD137) agonist antibody stimulates primary CD3+CD8+ T cell proliferation. FIGS. 2C and 2D show anti-4-1BB (anti-CD137) agonist antibody stimulates primary CD3+CD8− T cell proliferation.

Figure 3A:
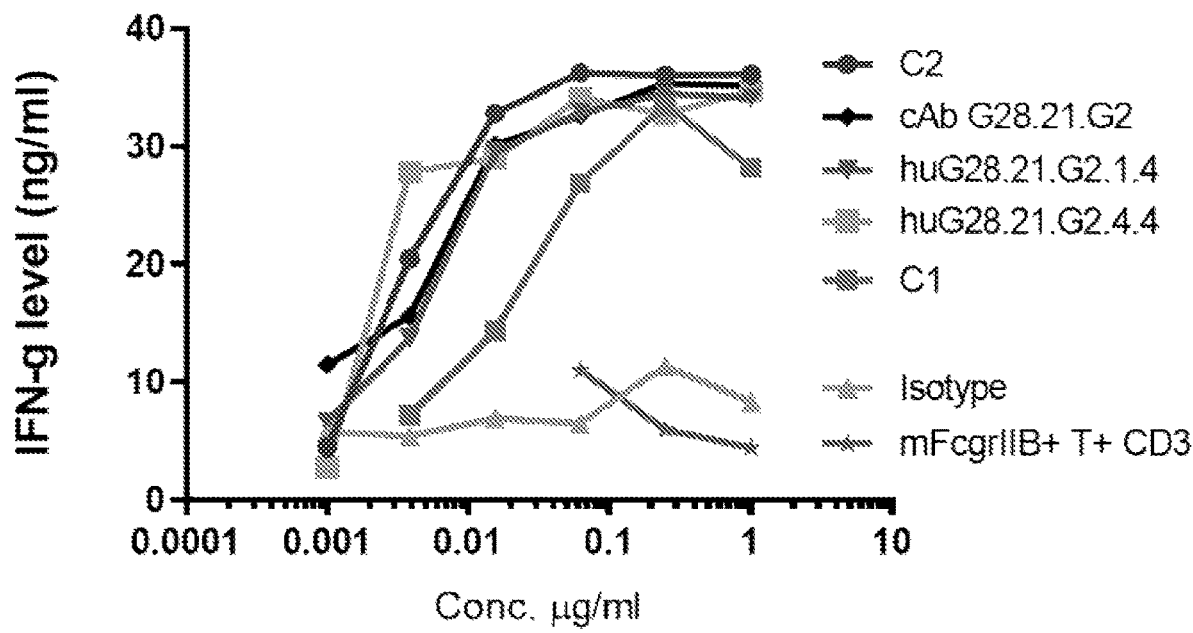
FIGS. 3A and 3B show anti-4-1BB (anti-CD137) agonist antibody of the present disclosure stimulates interferon-γ secretion.
Figure 3B:
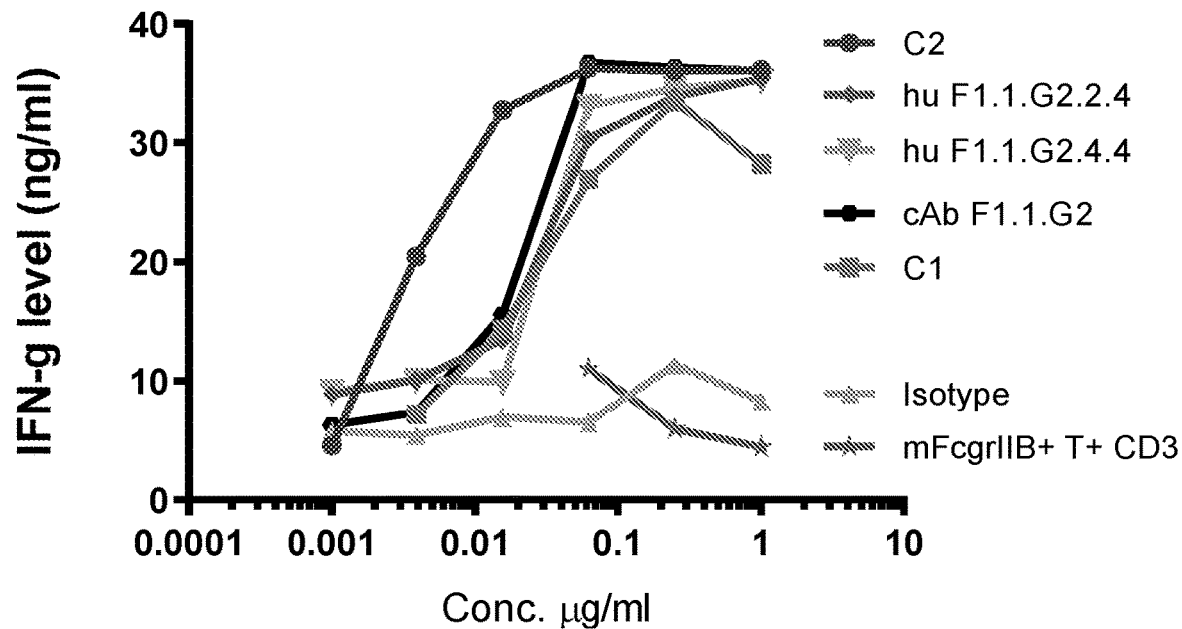

The cytokine (IFN-γ) release assay was similarly prepared without pan T cell labeling. Plates were incubated 48 hours in the 37° C. $CO_2$ incubator and culture supernatants were separated and collected onto two U-bottom 96-wells plates (70-80 μl/plate). For Elisa, culture supernatants were diluted 1:2 with Reagent diluent (R&D Systems, cat #DY995). Refer to R&D Systems Data Sheet and Assay Procedure (product #DY285B). FIGS. 3A and 3B show anti-4-1BB (anti-CD137) agonist antibody stimulates interferon-γ secretion.

MC38 Growth Inhibition in Transgenic Human 4-1BB Knock-In Mice

Figure 4A:
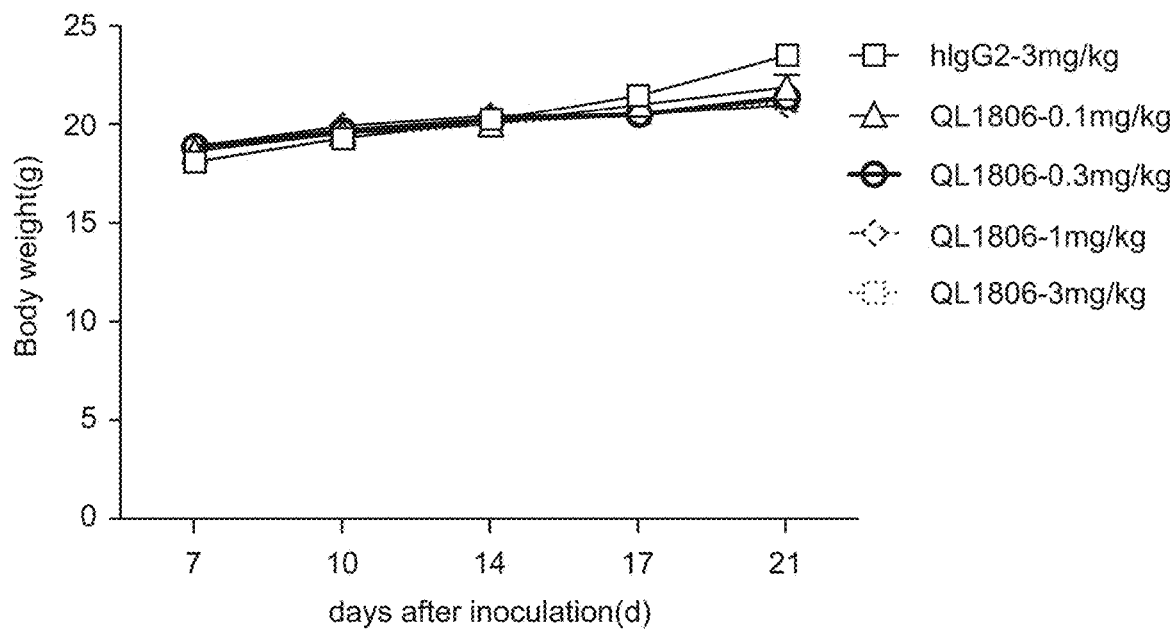
FIGS. 4A and 4B show anti-4-1BB (anti-CD137) agonist antibody of the present disclosure inhibits cancers in hu4-1BB knock-in mice.
Figure 4B:
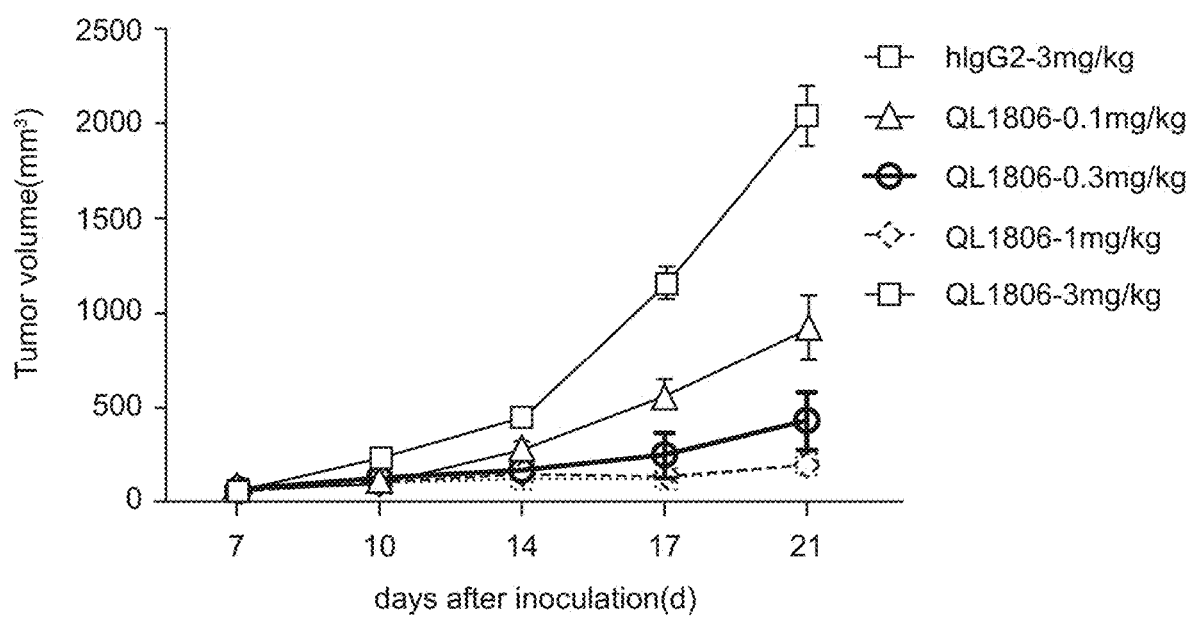

Mouse colon cancer MC38 cells were expanded in DMEM medium containing 10% fetal bovine serum, 1% penicillin and 1% streptomycin and 2 mM glutamine in a 37° C., 5% $CO_2$ incubator. 5E5 MC38 cells were seeded s.c. into the right armpit and tumors grew to 50-100 mm³ prior to administration of the test article. Per group, eight h4-1BB knock-in female mice were administered anti-4-1BB antibody at 0.1, 0.3, 1, or 3 mg/kg or hIgG2 at 3 mg/kg, i.p., twice per week for a total of 5 doses. FIG. 4A show that body weight of all test transgenic hu4-1BB knock-in mice gradually increased following administration of anti-4-1BB antibody. In addition, no drug-related toxicity was observed. QL1806 represents the anti-4-1BB antibody. FIG. 4B shows anti-4-1BB inhibits the growth of mouse colon cancer cells MC38. At day 21, significant inhibition (p<0.01) was observed and the 1 mg/kg and 3 mg/kg dose groups contained two tumor-free mice each (Table 5).

TABLE 5

Day 21 Tumor volume, inhibition rate, and tumor regression ( n = 8 )

| Group | Tumor volume (mm³) | TGI (%) | T/C (%) | Tumor free |
|---|---|---|---|---|
| hIgG2 (3 mg/kg) | 2048 ± 158.8 | / | / | 0/8 |
| QL1806 (0.1 mg/kg) | 935.8 ± 167.9 ** | 56.2 | 45.3 | 0/8 |
| QL1806 (0.3 mg/kg | 433.4 ± 152.4 ** | 81.5 | 21.6 | 1/8 |
| QL1806 (1 mg/kg) | 204.1 ± 84.5 ** | 93.1 | 9.91 | 2/8 |
| QL1806 (3 mg/kg) | 197.1 ± 50.9 ** | 93.5 | 9.62 | 2/8 |

Note:
Compared with hIgG2 (3 mg/kg group), * p < 0.05 ; ** p < 0.01.

The clone names (antibodies) shown in the figures, tables, and examples described herein comprise the heavy chain and light chain pairings shown in Table 6 below:

TABLE 6

Sequences for Clone Names

| Name | Heavy Chain SEQ ID NO | Light Chain SEQ ID NO |
|---|---|---|
| G28.21 | 2 | 1 |
| F1.1 | 36 | 35 |
| huG28.21.G2.1.4 | 32 | 33 |
| huG28.21.G2.4.4 | 34 | 33 |
| huF1.1.G2.2.4 | 48 | 46 |
| huF1.1.G2.4.4 | 50 | 46 |
| QL1806 | 34 | 33 |

SEQUENCE LISTING mouse
SEQ ID NO: 1
QIVLTQSPAIMSASLGERVTMTCTASSSVSSSYLHWYQQKPGSSPKLWI
YSTSNLASGVPARFSGSGSGTSYSLTISSMEAEDAATYYCHQYHRSPPT
FGSGTKLEIK
Underlined and bold: CDR1, 2 and 3, respectively (the same below), defined according to the Kabat numbering scheme.

SEQUENCE LISTING mouse
SEQ ID NO: 2
EVQLQQSGAELVRPGASVKLSCTASGFNIKDYYIHWVNQRPEQGLEWIG
RIDPEDGDIAYAPKFQDKATLTVDTSSNTAYLHIIGLTSEDTAVYYCTT
GNYYAMDFWGQGTSVTVSS.

Light chain CDRs
CDR1
TASSSVSSSYLH SEQ ID NO: 3 mouse

CDR2
STSNLA SEQ ID NO: 4 mouse

CDR3
HQYHRSPPT SEQ ID NO: 5 mouse

Heavy chain CDRs
CDR1
DYYIH SEQ ID NO: 6 mouse

CDR2
RIDPEDGDIAYAPKFQD SEQ ID NO: 7 mouse

CDR3
GNYYAMDF SEQ ID NO: 8 mouse

Humanized light chain variable domain
humanized mouse
SEQ ID NO: 9
EIVLTQSPATLSLSPGERVTLSCTASSSVSSSYLHWYQQKPGQSPRLWI
YSTSNLASGVPARFSGSGPGTSFTLTISSLEPEDFAVYYCHQYHRSPPT
FGQGTKLEIK humanized mouse
SEQ ID NO: 10
EIVLTQSPATLSLSPGERVTLSCTASSSVSSSYLHWYQQKPGSSPKLWI
YSTSNLASGVPARFSGSGPGTSFTLTISSLEPEDFAVYYCHQYHRSPPT
FGQGTKLEIK humanized mouse
SEQ ID NO: 11
EIVLTQSPATLSLSPGERVTLSCTASSSVSSSYLHWYQQKPGSSPKLWI
YSTSNLASGVPARFSGSGPGTSYTLTISSMEPEDFAVYYCHQYHRSPPT
FGQGTKLEIK humanized mouse
SEQ ID NO: 12
QIVLTQSPATLSASPGERVTLSCTASSSVSSSYLHWYQQKPGSSPKLWI
YSTSNLASGVPARFSGSGPGTSYTLTISSMEPEDAATYYCHQYHRSPPT
FGQGTKLEIK Humanized heavy chain variable domain
humanized mouse
SEQ ID NO: 13
EVQLVQSGAEVKKPGATVKISCKASGFNIKDYYIHWVNQAPGKGLEWIG
RIDPEDGDIAYAPKFQDRVTLTVDTSTDTAYLELSSLRSEDTAVYYCTT
GNYYAMDFWGQGTTVTVSS humanized mouse
SEQ ID NO: 14
EVQLVQSGAEVKKPGATVKLSCKASGFNIKDYYIHWVNQAPGKGLEWIG
RIDPEDGDIAYAPKFQDRATLTVDTSTNTAYLELSSLTSEDTAVYYCTT
GNYYAMDFWGQGTTVTVSS humanized mouse
SEQ ID NO: 15
EVQLQQSGAEVKKPGATVKLSCKASGFNIKDYYIHWVNQAPGKGLEWIG
RIDPEDGDIAYAPKFQDRATLTVDTSTNTAYLELSSLTSEDTAVYYCTT
GNYYAMDFWGQGTTVTVSS humanized mouse
SEQ ID NO: 16
EVQLQQSGAEVKKPGATVKLSCKASGFNIKDYYIHWVNQRPGQGLEWIG
RIDPEDGDIAYAPKFQDRATLTVDTSTNTAYLELSSLTSEDTAVYYCTT
GNYYAMDFWGQGTTVTVSS humanized mouse
SEQ ID NO: 17
EVQLQQSGAEVKKPGATVKLSCKASGFNIKDYYIHWVNQRPGQGLEWIG
RIDPEDGDIAYAPKFQDRATLTVDTSTNTAYLELSSLTSEDTAVYYCTT
GNYYAMDFWGQGTTVTVSS Humanized light chain variable domain
humanized mouse
SEQ ID NO: 18
EIVLTQSPDFQSVTPKEKVTITCRASSSVSYIHWYQQKPDSSPKAWIS**A
TSNLASGVPSRFSGSGSGTDFTLTINSLEAEDAATYYCQQWSSNPFT**FG
QGTKLEIK humanized mouse
SEQ ID NO: 19
EIVLTQSPDFQSATPKEKVTITCRASSSVSYIHWYQQKPDSSPKAWIS**A
TSNLAS**GVPSRFSGSGSGTSFTLTINSLEAEDAATYYCQQWSSNPFTFG
QGTKLEIK humanized mouse
SEQ ID NO: 20
EIVLTQSPDFQSATPKEKVTMTCRASSSVSYIHWYQQKPDSSPKAWIS**A
TSNLASGVPSRFSGSGSGTSYTLTINSVEAEDAATYYCQQWSSNPFT**FG
QGTKLEIK humanized mouse
SEQ ID NO: 21
EIVLTQSPDFQSATPKEKVTITCRASSSVSYIHWYQQKPGSSPKAWIS**A
TSNLASGVPSRFSGSGSGTSYTLTINRVEAEDAATYYCQQWSSNPFT**FG
QGTKLEIK Humanized heavy chain variable domain
humanized mouse
SEQ ID NO: 22
QVQLVQSGAEVKKPGASVKVSCKASGYTFTFYTMHWVRQAPGQGLEWIG
YINPSSGYTNYNQKFTDRVTLTADTSTSTAYMELSSLRSEDTAVYYCAR
SDGSSSKWYFDVWGQGTTVTVSS humanized mouse
SEQ ID NO: 23
QVQLVQSGAEVKKPGASVKVSCKASGYTFTFYTMHWLRQAPGQGLEWIG
YINPSSGYTNYNQKFTDRATLTADTSTSTAYMELSSLRSEDTAVYYCAR
SDGSSSKWYFDVWGQGTTVTVSS humanized mouse
SEQ ID NO: 24
QVQLVQSGAEVKKPGASVKMSCKASGYTFTFYTMHWLRQAPGQGLEWIG
YINPSSGYTNYNQKFTDRATLTADTSTSTAYMELSSLRSEDTAVYYCAR
SDGSSSKWYFDVWGQGTTVTVSS humanized mouse
SEQ ID NO: 25
QVQLVQSGAEVKKPGASVKMSCKASGYTFTFYTMHWLRQAPGQGLEWIG
YINPSSGYTNYNQKFTDRATLTADKSTSTAYMELSSLRSEDTAVYYCAR
SDGSSSKWYFDVWGQGTTVTVSS Light chain CDRs
CDR1
RASSSVSYIH SEQ ID NO: 26 mouse CDR2
ATSNLAS SEQ ID NO: 27 mouse CDR3
QQWSSNPFT SEQ ID NO: 28 mouse Heavy chain CDRs
CDR1
FYTMH SEQ ID NO: 29 mouse CDR2
YINPSSGYTNYNQKFTD SEQ ID NO: 30 mouse CDR3
SDGSSSKWYFDV SEQ ID NO: 31 mouse

SEQUENCE LISTING humanized mouse Fv, human Fc
SEQ ID NO: 32
EVQLVQSGAEVKKPGATVKISCKASGFNIKDYYIHWVNQAPGKGLEWIG
RIDPEDGDIAYAPKFQDRVTLTVDTSTDTAYLELSSLRSEDTAVYYCTT
GNYYAMDFWGQGTTVTVSSASTKGPSVFPLAPCSRSTSESTAALGCLVK
DYFPEPVTVSWNSGALTSGVHTFPAVLQSSGLYSLSSVVTVPSSNFGTQ
TYTCNVDHKPSNTKVDKTVERKCCVECPPCPAPPVAGPSVFLFPPKPKD
TLMISRTPEVTCVVVDVSHEDPEVQFNWYVDGVEVHNAKTKPREEQFNS
TFRVVSVLTVVHQDWLNGKEYKCKVSNKGLPAPIEKTISKTKGQPREPQ
VYTLPPSREEMTKNQVSLTCLVKGFYPSDIAVEWESNGQPENNYKTTPP
MLDSDGSFFLYSKLTVDKSRWQQGNVFSCSVMHEALHNHYTQKSLSLSP
GK humanized mouse Fv, human constant (Ckappa)
SEQ ID NO: 33
QIVLTQSPATLSASPGERVTLSCTASSSVSSSYLHWYQQKPGSSPKLWI
YSTSNLASGVPARFSGSGPGTSYTLTISSMEPEDAATYYCHQYHRSPPT
FGQGTKLEIKRTVAAPSVFIFPPSDEQLKSGTASVVCLLNNFYPREAKV
QWKVDNALQSGNSQESVTEQDSKDSTYSLSSTLTLSKADYEKHKVYACE
VTHQGLSSPVTKSFNRGEC humanized mouse Fv, human Fc
SEQ ID NO: 34
EVQLQQSGAEVKKPGATVKLSCKASGFNIKDYYIHWVNQRPGQGLEWIG
RIDPEDGDIAYAPKFQDRATLTVDTSTNTAYLELSSLRSEDTAVYYCTT
GNYYAMDFWGQGTTVTVSSASTKGPSVFPLAPCSRSTSESTAALGCLVK
DYFPEPVTVSWNSGALTSGVHTFPAVLQSSGLYSLSSVVTVPSSNFGTQ
TYTCNVDHKPSNTKVDKTVERKCCVECPPCPAPPVAGPSVFLFPPKPKD
TLMISRTPEVTCVVVDVSHEDPEVQFNWYVDGVEVHNAKTKPREEQFNS
TFRVVSVLTVVHQDWLNGKEYKCKVSNKGLPAPIEKTISKTKGQPREPQ
VYTLPPSREEMTKNQVSLTCLVKGFYPSDIAVEWESNGQPENNYKTTPP
MLDSDGSFFLYSKLTVDKSRWQQGNVFSCSVMHEALHNHYTQKSLSLSP
GK mouse
SEQ ID NO: 35
QIVLSQSPTILSASPGEKVTMTCRASSSVSYIHWYQQKPGSSPKAWISA
TSNLASGVPARFSGSGSGTSYSLTISRVEAEDAATYYCQQWSSNPFTFG
SGTKLEIK mouse
SEQ ID NO: 36
QVQLQQSGAELARPGASVKMSCKASGYTFTFYTMHWLKQRPGQGLEWIG
YINPSSGYTNYNQKFTDKATLTADKSSSTAYMQLSSLTSEDSAVYYCAR
SDGSSSKWYFDVWGTGTTVTVSS humanized mouse Fv, human constant (Ckappa)
SEQ ID NO: 37
EIVLTQSPATLSLSPGERVTLSCTASSSVSSSYLHWYQQKPGQSPRLWI
YSTSNLASGVPARFSGSGPGTSFTLTISSLEPEDFAVYYCHQYHRSPPT
FGQGTKLEIKRTVAAPSVFIFPPSDEQLKSGTASVVCLLNNFYPREAKV
QWKVDNALQSGNSQESVTEQDSKDSTYSLSSTLTLSKADYEKHKVYACE
VTHQGLSSPVTKSFNRGEC humanized mouse Fv, human constant (Ckappa)
SEQ ID NO: 38
EIVLTQSPATLSLSPGERVTLSCTASSSVSSSYLHWYQQKPGSSPKLWI
YSTSNLASGVPARFSGSGPGTSFTLTISSLEPEDFAVYYCHQYHRSPPT
FGQGTKLEIKRTVAAPSVFIFPPSDEQLKSGTASVVCLLNNFYPREAKV
QWKVDNALQSGNSQESVTEQDSKDSTYSLSSTLTLSKADYEKHKVYACE
VTHQGLSSPVTKSFNRGEC humanized mouse Fv, human constant (Ckappa)
SEQ ID NO: 39
EIVLTQSPATLSLSPGERVTLSCTASSSVSSSYLHWYQQKPGSSPKLWI
YSTSNLASGVPARFSGSGPGTSYTLTISSMEPEDFA VYYCHQYHRSPP
TFGQGTKLEIKRTVAAPSVFIFPPSDEQLKSGTASVVCLLNNFYPREAK
VQWKVDNALQSGNSQESVTEQDSKDSTYSLSSTLTLSKADYEKHKVYAC
EVTHQGLSSPVTKSFNRGEC humanized mouse Fv, human Fc
SEQ ID NO: 40
EVQLQQSGAEVKKPGATVKLSCKASGFNIKDYYIHWVNQAPGKGLEWIG
RIDPEDGDIAYAPKFQDRATLTVDTSTNTAYLELSSLTSEDTAVYYCTT
GNYYAMDFWGQGTTVTVSSASTKGPSVFPLAPCSRSTSESTAALGCLVK
DYFPEPVTVSWNSGALTSGVHTFPAVLQSSGLYSLSSVVTVPSSNFGTQ
TYTCNVDHKPSNTKVDKTVERKCCVECPPCPAPPVAGPSVFLFPPKPKD
TLMISRTPEVTCVVVDVSHEDPEVQFNWYVDGVEVHNAKTKPREEQFNS
TFRVVSVLTVVHQDWLNGKEYKCKVSNKGLPAPIEKTISKTKGQPREPQ
VYTLPPSREEMTKNQVSLTCLVKGFYPSDIAVEWESNGQPENNYKTTPP
MLDSDGSFFLYSKLTVDKSRWQQGNVFSCSVMHEALHNHYTQKSLSLSP
GK humanized mouse Fv, human Fc
SEQ ID NO: 41
EVQLQQSGAEVKKPGATVKLSCKASGFNIKDYYIHWVNQAPGKGLEWIG
RIDPEDGDIAYAPKFQDRATLTVDTSTNTAYLELSSLRSEDTAVYYCTT
GNYYAMDFWGQGTTVTVSSASTKGPSVFPLAPCSRSTSESTAALGCLVK
DYFPEPVTVSWNSGALTSGVHTFPAVLQSSGLYSLSSVVTVPSSNFGTQ
TYTCNVDHKPSNTKVDKTVERKCCVECPPCPAPPVAGPSVFLFPPKPKD
TLMISRTPEVTCVVVDVSHEDPEVQFNWYVDGVEVHNAKTKPREEQFNS
TFRVVSVLTVVHQDWLNGKEYKCKVSNKGLPAPIEKTISKTKGQPREPQ
VYTLPPSREEMTKNQVSLTCLVKGFYPSDIAVEWESNGQPENNYKTTPP
MLDSDGSFFLYSKLTVDKSRWQQGNVFSCSVMHEALHNHYTQKSLSLSP
GK humanized mouse Fv, human Fc
SEQ ID NO: 42
EVQLQQSGAEVKKPGATVKLSCKASGFNIKDYYIHWVNQRPGQGLEWIG
RIDPEDGDIAYAPKFQDRATLTVDTSTNTAYLELSSLTSEDTAVYYCTT
GNYYAMDFWGQGTTVTVSSASTKGPSVFPLAPCSRSTSESTAALGCLVK
DYFPEPVTVSWNSGALTSGVHTFPAVLQSSGLYSLSSVVTVPSSNFGTQ
TYTCNVDHKPSNTKVDKTVERKCCVECPPCPAPPVAGPSVFLFPPKPKD
TLMISRTPEVTCVVVDVSHEDPEVQFNWYVDGVEVHNAKTKPREEQFNS
TFRVVSVLTVVHQDWLNGKEYKCKVSNKGLPAPIEKTISKTKGQPREPQ
VYTLPPSREEMTKNQVSLTCLVKGFYPSDIAVEWESNGQPENNYKTTPP
MLDSDGSFFLYSKLTVDKSRWQQGNVFSCSVMHEALHNHYTQKSLSLSP
GK humanized mouse Fv, human constant (Ckappa)
SEQ ID NO: 43
EIVLTQSPDFQSVTPKEKVTITCRASSSVSYIHWYQQKPDSSPKAWISA
TSNLASGVPSRFSGSGSGTDFTLTINSLEAEDAATYYCQQWSSNPFTFG
QGTKLEIKRTVAAPSVFIFPPSDEQLKSGTASVVCLLNNFYPREAKVQW
KVDNALQSGNSQESVTEQDSKDSTYSLSSTLTLSKADYEKHKVYACEVT
HQGLSSPVTKSFNRGEC humanized mouse Fv, human constant (Ckappa)
SEQ ID NO: 44
EIVLTQSPDFQSATPKEKVTITCRASSSVSYIHWYQQKPDSSPKAWISA
TSNLASGVPSRFSGSGSGTSFTLTINSLEAEDAATYYCQQWSSNPFTFG
QGTKLEIKRTVAAPSVFIFPPSDEQLKSGTASVVCLLNNFYPREAKVQW
KVDNALQSGNSQESVTEQDSKDSTYSLSSTLTLSKADYEKHKVYACEVT
HQGLSSPVTKSFNRGEC humanized mouse Fv, human constant (Ckappa)
SEQ ID NO: 45
EIVLTQSPDFQSATPKEKVTMTCRASSSVSYIHWYQQKPDSSPKAWISA
TSNLASGVPSRFSGSGSGTSYTLTINSVEAEDAATYYCQQWSSNPFTFG
QGTKLEIKRTVAAPSVFIFPPSDEQLKSGTASVVCLLNNFYPREAKVQW
KVDNALQSGNSQESVTEQDSKDSTYSLSSTLTLSKADYEKHKVYACEVT
HQGLSSPVTKSFNRGEC humanized mouse Fv, human constant (Ckappa)
SEQ ID NO: 46
EIVLTQSPDFQSATPKEKVTITCRASSSVSYIHWYQQKPGSSPKAWISA
TSNLASGVPSRFSGSGSGTSYTLTINRVEAEDAATYYCQQWSSNPFTFG
QGTKLEIKRTVAAPSVFIFPPSDEQLKSGTASVVCLLNNFYPREAKVQW
KVDNALQSGNSQESVTEQDSKDSTYSLSSTLTLSKADYEKHKVYACEVT
HQGLSSPVTKSFNRGEC humanized mouse Fv, human Fc
SEQ ID NO: 47
QVQLVQSGAEVKKPGASVKVSCKASGYTFTFYTMHWVRAPGQGLEWIG
YINPSSGYTNYNQKFTDRVTLTADTSTSTAYMELSSLRSEDTAVYYCAR
SDGSSSKWYFDVWGQGTTVTVSSASTKGPSVFPLAPCSRSTSESTAALG
CLVKDYFPEPVTVSWNSGALTSGVHTFPAVLQSSGLYSLSSVVTVPSSN
FGTQTYTCNVDHKPSNTKVDKTVERKCCVECPPCPAPPVAGPSVFLFPP
KPKDTLMISRTPEVTCVVVDVSHEDPEVQFNWYVDGVEVHNAKTKPREE
QFNSTFRVVSVLTVVHQDWLNGKEYKCKVSNKGLPAPIEKTISKTKGQP
REPQVYTLPPSREEMTKNQVSLTCLVKGFYPSDIAVEWESNGQPENNYK
TTPPMLDSDGSFFLYSKLTVDKSRWQQGNVFSCSVMHEALHNHYTQKSL
SLSPGK

SEQUENCE LISTING humanized mouse Fv, human Fc
SEQ ID NO: 48
QVQLVQSGAEVKKPGASVKVSCKASGYTFTFYTMHWLRQAPGQGLEWIG
YINPSSGYTNYNQKFTDRATLTADTSTSTAYMELSSLRSEDTAVYYCAR
SDGSSSKWYFDVWGQGTTVTVSSASTKGPSVFPLAPCSRSTSESTAALG
CLVKDYFPEPVTVSWNSGALTSGVHTFPAVLQSSGLYSLSSVVTVPSSN
FGTQTYTCNVDHKPSNTKVDKTVERKCCVECPPCPAPPVAGPSVFLFPP
KPKDTLMISRTPEVTCVVVDVSHEDPEVQFNWYVDGVEVHNAKTKPREE
QFNSTFRVVSVLTVVHQDWLNGKEYKCKVSNKGLPAPIEKTISKTKGQP
REPQVYTLPPSREEMTKNQVSLTCLVKGFYPSDIAVEWESNGQPENNYK
TTPPMLDSDGSFFLYSKLTVDKSRWQQGNVFSCSVMHEALHNHYTQKSL
SLSPGK humanized mouse Fv, human Fc
SEQ ID NO: 49
QVQLVQSGAEVKKPGASVKMSCKASGYTFTFYTMHWLKQAPGQGLEWIG
YINPSSGYTNYNQKFTDRATLTADTSTSTAYMELSSLRSEDTAVYYCAR
SDGSSSKWYFDVWGQGTTVTVSSASTKGPSVFPLAPCSRSTSESTAALG
CLVKDYFPEPVTVSWNSGALTSGVHTFPAVLQSSGLYSLSSVVTVPSSN
FGTQTYTCNVDHKPSNTKVDKTVERKCCVECPPCPAPPVAGPSVFLFPP
KPKDTLMISRTPEVTCVVVDVSHEDPEVQFNWYVDGVEVHNAKTKPREE
QFNSTFRVVSVLTVVHQDWLNGKEYKCKVSNKGLPAPIEKTISKTKGQP
REPQVYTLPPSREEMTKNQVSLTCLVKGFYPSDIAVEWESNGQPENNYK
TTPPMLDSDGSFFLYSKLTVDKSRWQQGNVFSCSVMHEALHNHYTQKSL
SLSPGK humanized mouse Fv, human Fc
SEQ ID NO: 50
QVQLVQSGAEVKKPGASVKMSCKASGYTFTFYTMHWLKQAPGQGLEWIG
YINPSSGYTNYNQKFTDRATLTADKSTSTAYMELSSLRSEDTAVYYCAR
SDGSSSKWYFDVWGQGTTVTVSSASTKGPSVFPLAPCSRSTSESTAALG
CLVKDYFPEPVTVSWNSGALTSGVHTFPAVLQSSGLYSLSSVVTVPSSN
FGTQTYTCNVDHKPSNTKVDKTVERKCCVECPPCPAPPVAGPSVFLFPP
KPKDTLMISRTPEVTCVVVDVSHEDPEVQFNWYVDGVEVHNAKTKPREE
QFNSTFRVVSVLTVVHQDWLNGKEYKCKVSNKGLPAPIEKTISKTKGQP
REPQVYTLPPSREEMTKNQVSLTCLVKGFYPSDIAVEWESNGQPENNYK
TTPPMLDSDGSFFLYSKLTVDKSRWQQGNVFSCSVMHEALHNHYTQKSL
SLSPGK

---

We claim:

1. An isolated anti-CD137 agonist antibody, or an antigen-binding portion thereof, comprising:
   a heavy chain variable region CDR1 comprising SEQ ID NO:29, a heavy chain variable region CDR2 comprising SEQ ID NO:30, and a heavy chain variable region CDR3 comprising SEQ ID NO:31; and
   a light chain variable region CDR1 comprising SEQ ID NO:26, a light chain variable region CDR2 comprising SEQ ID NO:27, and a light chain variable region CDR3 comprising SEQ ID NO:28;
   wherein said antibody or portion specifically binds to human CD137.

2. The isolated antibody, or antigen-binding portion thereof, of claim 1, which comprises a light chain variable region amino acid sequence having at least 95% identity to SEQ ID NO: 35 and a heavy chain variable region amino acid sequence having at least 95% identity to SEQ ID NO:36.

3. The isolated antibody, or an antigen-binding portion thereof, of claim 1, which comprises a heavy chain variable region comprising an amino acid sequence that has at least 95%, at least 96%, at least 97%, at least 98%, or at least 99% identical to a sequence as set forth in SEQ ID NO:36.

4. The isolated antibody, or antigen-binding portion thereof, of claim 1, which is a Fab fragment, an F(ab')$_2$ fragment, an Fv fragment, a single chain antibody, or a bispecific antibody.

5. The isolated antibody of claim 1, which is a chimeric antibody or humanized antibody.

6. The isolated antibody of claim 1, which is an immunoglobulin G (IgG), an IgM, an IgE, an IgA or an IgD molecule.

7. The isolated antibody of claim 6, which is an IgG1, IgG2, IgG3, or IgG4.

8. The isolated antibody, or antigen-binding portion thereof, of claim 1, which comprises: heavy chain variable region comprising an amino acid sequence selected from the group consisting of SEQ ID NOs: 22-25 and a light chain variable region comprising an amino acid sequence selected from the group consisting of SEQ ID NOs: 18-21.

9. The isolated antibody of claim 8, which is a chimeric antibody or humanized antibody.

10. The isolated antibody of claim 8, which is an immunoglobulin G (IgG), an IgM, an IgE, an IgA or an IgD molecule.

11. The isolated antibody of claim 10, which is an IgG1, IgG2, IgG3, or IgG4.

12. The isolated antibody claim 1, wherein the antibody is monoclonal.

13. An isolated monoclonal antibody or antigen binding portion thereof, comprising a light chain comprising an amino acid sequence selected from the group consisting of SEQ ID NOs: 43-46 and a heavy chain comprising an amino acid sequence selected from the group consisting of SEQ ID NOs: 47-50.

14. An immunoconjugate comprising the antibody, or antigen-binding portion thereof, of claim 1, linked to a therapeutic agent.

15. A pharmaceutical composition comprising the antibody, or antigen-binding portion thereof, according to claim 1, and a pharmaceutically acceptable carrier.

16. A method of stimulating immune responses in a subject, comprising the step of administering to the subject the pharmaceutical composition according to claim 15 in therapeutically effective amount to stimulate an immune response in said subject.

17. A method of treating colon cancer in a subject, comprising the step of administering to the subject the pharmaceutical composition according to claim 15 in therapeutically effective amount to treat said cancer.

* * * * *

SEQUENCE LISTING

<160> NUMBER OF SEQ ID NOS: 50

<210> SEQ ID NO 1
<211> LENGTH: 108
<212> TYPE: PRT
<213> ORGANISM: Mus musculus
<400> SEQUENCE: 1

```
Gln Ile Val Leu Thr Gln Ser Pro Ala Ile Met Ser Ala Ser Leu Gly
1               5                   10                  15

Glu Arg Val Thr Met Thr Cys Thr Ala Ser Ser Ser Val Ser Ser Ser
            20                  25                  30

Tyr Leu His Trp Tyr Gln Gln Lys Pro Gly Ser Ser Pro Lys Leu Trp
        35                  40                  45

Ile Tyr Ser Thr Ser Asn Leu Ala Ser Gly Val Pro Ala Arg Phe Ser
    50                  55                  60

Gly Ser Gly Ser Gly Thr Ser Tyr Ser Leu Thr Ile Ser Ser Met Glu
65                  70                  75                  80

Ala Glu Asp Ala Ala Thr Tyr Tyr Cys His Gln Tyr His Arg Ser Pro
                85                  90                  95

Pro Thr Phe Gly Ser Gly Thr Lys Leu Glu Ile Lys
            100                 105
```

<210> SEQ ID NO 2
<211> LENGTH: 117
<212> TYPE: PRT
<213> ORGANISM: Mus musculus
<400> SEQUENCE: 2

```
Glu Val Gln Leu Gln Gln Ser Gly Ala Glu Leu Val Arg Pro Gly Ala
1               5                   10                  15

Ser Val Lys Leu Ser Cys Thr Ala Ser Gly Phe Asn Ile Lys Asp Tyr
            20                  25                  30

Tyr Ile His Trp Val Asn Gln Arg Pro Glu Gln Gly Leu Glu Trp Ile
        35                  40                  45

Gly Arg Ile Asp Pro Glu Asp Gly Asp Ile Ala Tyr Ala Pro Lys Phe
    50                  55                  60

Gln Asp Lys Ala Thr Leu Thr Val Asp Thr Ser Ser Asn Thr Ala Tyr
```

```
                65                  70                  75                  80
Leu His Ile Ile Gly Leu Thr Ser Glu Asp Thr Ala Val Tyr Tyr Cys
                        85                  90                  95
Thr Thr Gly Asn Tyr Tyr Ala Met Asp Phe Trp Gly Gln Gly Thr Ser
                100                 105                 110
Val Thr Val Ser Ser
            115

<210> SEQ ID NO 3
<211> LENGTH: 12
<212> TYPE: PRT
<213> ORGANISM: Mus musculus

<400> SEQUENCE: 3

Thr Ala Ser Ser Ser Val Ser Ser Ser Tyr Leu His
1               5                   10

<210> SEQ ID NO 4
<211> LENGTH: 6
<212> TYPE: PRT
<213> ORGANISM: Mus musculus

<400> SEQUENCE: 4

Ser Thr Ser Asn Leu Ala
1               5

<210> SEQ ID NO 5
<211> LENGTH: 9
<212> TYPE: PRT
<213> ORGANISM: Mus musculus

<400> SEQUENCE: 5

His Gln Tyr His Arg Ser Pro Pro Thr
1               5

<210> SEQ ID NO 6
<211> LENGTH: 5
<212> TYPE: PRT
<213> ORGANISM: Mus musculus

<400> SEQUENCE: 6

Asp Tyr Tyr Ile His
1               5

<210> SEQ ID NO 7
<211> LENGTH: 17
<212> TYPE: PRT
<213> ORGANISM: Mus musculus

<400> SEQUENCE: 7

Arg Ile Asp Pro Glu Asp Gly Asp Ile Ala Tyr Ala Pro Lys Phe Gln
1               5                   10                  15

Asp

<210> SEQ ID NO 8
<211> LENGTH: 8
<212> TYPE: PRT
<213> ORGANISM: Mus musculus

<400> SEQUENCE: 8

Gly Asn Tyr Tyr Ala Met Asp Phe
1               5
```

<210> SEQ ID NO 9
<211> LENGTH: 108
<212> TYPE: PRT
<213> ORGANISM: Artificial Sequence
<220> FEATURE:
<223> OTHER INFORMATION: humanized mouse IgG

<400> SEQUENCE: 9

```
Glu Ile Val Leu Thr Gln Ser Pro Ala Thr Leu Ser Leu Ser Pro Gly
1               5                   10                  15

Glu Arg Val Thr Leu Ser Cys Thr Ala Ser Ser Val Ser Ser Ser
            20                  25                  30

Tyr Leu His Trp Tyr Gln Gln Lys Pro Gly Ser Pro Arg Leu Trp
        35                  40                  45

Ile Tyr Ser Thr Ser Asn Leu Ala Ser Gly Val Pro Ala Arg Phe Ser
    50                  55                  60

Gly Ser Gly Pro Gly Thr Ser Phe Thr Leu Thr Ile Ser Ser Leu Glu
65                  70                  75                  80

Pro Glu Asp Phe Ala Val Tyr Tyr Cys His Gln Tyr His Arg Ser Pro
                85                  90                  95

Pro Thr Phe Gly Gln Gly Thr Lys Leu Glu Ile Lys
            100                 105
```

<210> SEQ ID NO 10
<211> LENGTH: 108
<212> TYPE: PRT
<213> ORGANISM: Artificial Sequence
<220> FEATURE:
<223> OTHER INFORMATION: humanized mouse IgG

<400> SEQUENCE: 10

```
Glu Ile Val Leu Thr Gln Ser Pro Ala Thr Leu Ser Leu Ser Pro Gly
1               5                   10                  15

Glu Arg Val Thr Leu Ser Cys Thr Ala Ser Ser Val Ser Ser Ser
            20                  25                  30

Tyr Leu His Trp Tyr Gln Gln Lys Pro Gly Ser Ser Pro Lys Leu Trp
        35                  40                  45

Ile Tyr Ser Thr Ser Asn Leu Ala Ser Gly Val Pro Ala Arg Phe Ser
    50                  55                  60

Gly Ser Gly Pro Gly Thr Ser Phe Thr Leu Thr Ile Ser Ser Leu Glu
65                  70                  75                  80

Pro Glu Asp Phe Ala Val Tyr Tyr Cys His Gln Tyr His Arg Ser Pro
                85                  90                  95

Pro Thr Phe Gly Gln Gly Thr Lys Leu Glu Ile Lys
            100                 105
```

<210> SEQ ID NO 11
<211> LENGTH: 108
<212> TYPE: PRT
<213> ORGANISM: Artificial Sequence
<220> FEATURE:
<223> OTHER INFORMATION: humanized mouse IgG

<400> SEQUENCE: 11

```
Glu Ile Val Leu Thr Gln Ser Pro Ala Thr Leu Ser Leu Ser Pro Gly
1               5                   10                  15

Glu Arg Val Thr Leu Ser Cys Thr Ala Ser Ser Val Ser Ser Ser
            20                  25                  30

Tyr Leu His Trp Tyr Gln Gln Lys Pro Gly Ser Ser Pro Lys Leu Trp
```

```
                    35                  40                  45

Ile Tyr Ser Thr Ser Asn Leu Ala Ser Gly Val Pro Ala Arg Phe Ser
 50                  55                  60

Gly Ser Gly Pro Gly Thr Ser Tyr Thr Leu Thr Ile Ser Ser Met Glu
 65                  70                  75                  80

Pro Glu Asp Phe Ala Val Tyr Tyr Cys His Gln Tyr His Arg Ser Pro
                 85                  90                  95

Pro Thr Phe Gly Gln Gly Thr Lys Leu Glu Ile Lys
            100                 105
```

<210> SEQ ID NO 12
<211> LENGTH: 108
<212> TYPE: PRT
<213> ORGANISM: Artificial Sequence
<220> FEATURE:
<223> OTHER INFORMATION: humanized mouse IgG

<400> SEQUENCE: 12

```
Gln Ile Val Leu Thr Gln Ser Pro Ala Thr Leu Ser Ala Ser Pro Gly
 1                   5                  10                  15

Glu Arg Val Thr Leu Ser Cys Thr Ala Ser Ser Val Ser Ser Ser
                 20                  25                  30

Tyr Leu His Trp Tyr Gln Gln Lys Pro Gly Ser Ser Pro Lys Leu Trp
                 35                  40                  45

Ile Tyr Ser Thr Ser Asn Leu Ala Ser Gly Val Pro Ala Arg Phe Ser
 50                  55                  60

Gly Ser Gly Pro Gly Thr Ser Tyr Thr Leu Thr Ile Ser Ser Met Glu
 65                  70                  75                  80

Pro Glu Asp Ala Ala Thr Tyr Tyr Cys His Gln Tyr His Arg Ser Pro
                 85                  90                  95

Pro Thr Phe Gly Gln Gly Thr Lys Leu Glu Ile Lys
            100                 105
```

<210> SEQ ID NO 13
<211> LENGTH: 117
<212> TYPE: PRT
<213> ORGANISM: Artificial Sequence
<220> FEATURE:
<223> OTHER INFORMATION: humanized mouse IgG

<400> SEQUENCE: 13

```
Glu Val Gln Leu Val Gln Ser Gly Ala Glu Val Lys Lys Pro Gly Ala
 1                   5                  10                  15

Thr Val Lys Ile Ser Cys Lys Ala Ser Gly Phe Asn Ile Lys Asp Tyr
                 20                  25                  30

Tyr Ile His Trp Val Asn Gln Ala Pro Gly Lys Gly Leu Glu Trp Ile
                 35                  40                  45

Gly Arg Ile Asp Pro Glu Asp Gly Asp Ile Ala Tyr Ala Pro Lys Phe
 50                  55                  60

Gln Asp Arg Val Thr Leu Thr Val Asp Thr Ser Thr Asp Thr Ala Tyr
 65                  70                  75                  80

Leu Glu Leu Ser Ser Leu Arg Ser Glu Asp Thr Ala Val Tyr Tyr Cys
                 85                  90                  95

Thr Thr Gly Asn Tyr Tyr Ala Met Asp Phe Trp Gly Gln Gly Thr Thr
                100                 105                 110

Val Thr Val Ser Ser
            115
```

<210> SEQ ID NO 14
<211> LENGTH: 117
<212> TYPE: PRT
<213> ORGANISM: Artificial Sequence
<220> FEATURE:
<223> OTHER INFORMATION: humanized mouse IgG

<400> SEQUENCE: 14

Glu Val Gln Leu Val Gln Ser Gly Ala Glu Val Lys Lys Pro Gly Ala
1               5                   10                  15

Thr Val Lys Leu Ser Cys Lys Ala Ser Gly Phe Asn Ile Lys Asp Tyr
            20                  25                  30

Tyr Ile His Trp Val Asn Gln Ala Pro Gly Lys Gly Leu Glu Trp Ile
        35                  40                  45

Gly Arg Ile Asp Pro Glu Asp Gly Asp Ile Ala Tyr Ala Pro Lys Phe
    50                  55                  60

Gln Asp Arg Ala Thr Leu Thr Val Asp Thr Ser Thr Asn Thr Ala Tyr
65                  70                  75                  80

Leu Glu Leu Ser Ser Leu Thr Ser Glu Asp Thr Ala Val Tyr Tyr Cys
                85                  90                  95

Thr Thr Gly Asn Tyr Tyr Ala Met Asp Phe Trp Gly Gln Gly Thr Thr
            100                 105                 110

Val Thr Val Ser Ser
        115

<210> SEQ ID NO 15
<211> LENGTH: 117
<212> TYPE: PRT
<213> ORGANISM: Artificial Sequence
<220> FEATURE:
<223> OTHER INFORMATION: humanized mouse IgG

<400> SEQUENCE: 15

Glu Val Gln Leu Gln Gln Ser Gly Ala Glu Val Lys Lys Pro Gly Ala
1               5                   10                  15

Thr Val Lys Leu Ser Cys Lys Ala Ser Gly Phe Asn Ile Lys Asp Tyr
            20                  25                  30

Tyr Ile His Trp Val Asn Gln Ala Pro Gly Lys Gly Leu Glu Trp Ile
        35                  40                  45

Gly Arg Ile Asp Pro Glu Asp Gly Asp Ile Ala Tyr Ala Pro Lys Phe
    50                  55                  60

Gln Asp Arg Ala Thr Leu Thr Val Asp Thr Ser Thr Asn Thr Ala Tyr
65                  70                  75                  80

Leu Glu Leu Ser Ser Leu Arg Ser Glu Asp Thr Ala Val Tyr Tyr Cys
                85                  90                  95

Thr Thr Gly Asn Tyr Tyr Ala Met Asp Phe Trp Gly Gln Gly Thr Thr
            100                 105                 110

Val Thr Val Ser Ser
        115

<210> SEQ ID NO 16
<211> LENGTH: 117
<212> TYPE: PRT
<213> ORGANISM: Artificial Sequence
<220> FEATURE:
<223> OTHER INFORMATION: humanized mouse IgG

<400> SEQUENCE: 16

Glu Val Gln Leu Gln Gln Ser Gly Ala Glu Val Lys Lys Pro Gly Ala

```
                1               5                   10                  15
        Thr Val Lys Leu Ser Cys Lys Ala Ser Gly Phe Asn Ile Lys Asp Tyr
                        20                  25                  30

Tyr Ile His Trp Val Asn Gln Arg Pro Gly Gln Gly Leu Glu Trp Ile
                        35                  40                  45

Gly Arg Ile Asp Pro Glu Asp Gly Asp Ile Ala Tyr Ala Pro Lys Phe
                50                  55                  60

Gln Asp Arg Ala Thr Leu Thr Val Asp Thr Ser Thr Asn Thr Ala Tyr
        65                  70                  75                  80

Leu Glu Leu Ser Ser Leu Arg Ser Glu Asp Thr Ala Val Tyr Tyr Cys
                        85                  90                  95

Thr Thr Gly Asn Tyr Tyr Ala Met Asp Phe Trp Gly Gln Gly Thr Thr
                        100                 105                 110

Val Thr Val Ser Ser
                        115

<210> SEQ ID NO 17
<211> LENGTH: 117
<212> TYPE: PRT
<213> ORGANISM: Artificial Sequence
<220> FEATURE:
<223> OTHER INFORMATION: humanized mouse IgG

<400> SEQUENCE: 17

Glu Val Gln Leu Gln Gln Ser Gly Ala Glu Val Lys Lys Pro Gly Ala
        1               5                   10                  15

Thr Val Lys Leu Ser Cys Lys Ala Ser Gly Phe Asn Ile Lys Asp Tyr
                        20                  25                  30

Tyr Ile His Trp Val Asn Gln Arg Pro Gly Gln Gly Leu Glu Trp Ile
                        35                  40                  45

Gly Arg Ile Asp Pro Glu Asp Gly Asp Ile Ala Tyr Ala Pro Lys Phe
                50                  55                  60

Gln Asp Arg Ala Thr Leu Thr Val Asp Thr Ser Thr Asn Thr Ala Tyr
        65                  70                  75                  80

Leu Glu Leu Ser Ser Leu Thr Ser Glu Asp Thr Ala Val Tyr Tyr Cys
                        85                  90                  95

Thr Thr Gly Asn Tyr Tyr Ala Met Asp Phe Trp Gly Gln Gly Thr Thr
                        100                 105                 110

Val Thr Val Ser Ser
                        115

<210> SEQ ID NO 18
<211> LENGTH: 106
<212> TYPE: PRT
<213> ORGANISM: Artificial Sequence
<220> FEATURE:
<223> OTHER INFORMATION: humanized mouse IgG

<400> SEQUENCE: 18

Glu Ile Val Leu Thr Gln Ser Pro Asp Phe Gln Ser Val Thr Pro Lys
        1               5                   10                  15

Glu Lys Val Thr Ile Thr Cys Arg Ala Ser Ser Ser Val Ser Tyr Ile
                        20                  25                  30

His Trp Tyr Gln Gln Lys Pro Asp Ser Ser Pro Lys Ala Trp Ile Ser
                        35                  40                  45

Ala Thr Ser Asn Leu Ala Ser Gly Val Pro Ser Arg Phe Ser Gly Ser
                50                  55                  60
```

```
Gly Ser Gly Thr Asp Phe Thr Leu Thr Ile Asn Ser Leu Glu Ala Glu
65                  70                  75                  80

Asp Ala Ala Thr Tyr Tyr Cys Gln Gln Trp Ser Ser Asn Pro Phe Thr
                85                  90                  95

Phe Gly Gln Gly Thr Lys Leu Glu Ile Lys
            100                 105
```

<210> SEQ ID NO 19
<211> LENGTH: 106
<212> TYPE: PRT
<213> ORGANISM: Artificial Sequence
<220> FEATURE:
<223> OTHER INFORMATION: humanized mouse IgG

<400> SEQUENCE: 19

```
Glu Ile Val Leu Thr Gln Ser Pro Asp Phe Gln Ser Ala Thr Pro Lys
1               5                   10                  15

Glu Lys Val Thr Ile Thr Cys Arg Ala Ser Ser Val Ser Tyr Ile
                20                  25                  30

His Trp Tyr Gln Gln Lys Pro Asp Ser Ser Pro Lys Ala Trp Ile Ser
            35                  40                  45

Ala Thr Ser Asn Leu Ala Ser Gly Val Pro Ser Arg Phe Ser Gly Ser
        50                  55                  60

Gly Ser Gly Thr Ser Phe Thr Leu Thr Ile Asn Ser Leu Glu Ala Glu
65                  70                  75                  80

Asp Ala Ala Thr Tyr Tyr Cys Gln Gln Trp Ser Ser Asn Pro Phe Thr
                85                  90                  95

Phe Gly Gln Gly Thr Lys Leu Glu Ile Lys
            100                 105
```

<210> SEQ ID NO 20
<211> LENGTH: 106
<212> TYPE: PRT
<213> ORGANISM: Artificial Sequence
<220> FEATURE:
<223> OTHER INFORMATION: humanized mouse IgG

<400> SEQUENCE: 20

```
Glu Ile Val Leu Thr Gln Ser Pro Asp Phe Gln Ser Ala Thr Pro Lys
1               5                   10                  15

Glu Lys Val Thr Met Thr Cys Arg Ala Ser Ser Val Ser Tyr Ile
                20                  25                  30

His Trp Tyr Gln Gln Lys Pro Asp Ser Ser Pro Lys Ala Trp Ile Ser
            35                  40                  45

Ala Thr Ser Asn Leu Ala Ser Gly Val Pro Ser Arg Phe Ser Gly Ser
        50                  55                  60

Gly Ser Gly Thr Ser Tyr Thr Leu Thr Ile Asn Ser Val Glu Ala Glu
65                  70                  75                  80

Asp Ala Ala Thr Tyr Tyr Cys Gln Gln Trp Ser Ser Asn Pro Phe Thr
                85                  90                  95

Phe Gly Gln Gly Thr Lys Leu Glu Ile Lys
            100                 105
```

<210> SEQ ID NO 21
<211> LENGTH: 106
<212> TYPE: PRT
<213> ORGANISM: Artificial Sequence
<220> FEATURE:
<223> OTHER INFORMATION: humanized mouse IgG

<400> SEQUENCE: 21

Glu Ile Val Leu Thr Gln Ser Pro Asp Phe Gln Ser Ala Thr Pro Lys
1               5                   10                  15

Glu Lys Val Thr Ile Thr Cys Arg Ala Ser Ser Ser Val Ser Tyr Ile
            20                  25                  30

His Trp Tyr Gln Gln Lys Pro Gly Ser Ser Pro Lys Ala Trp Ile Ser
        35                  40                  45

Ala Thr Ser Asn Leu Ala Ser Gly Val Pro Ser Arg Phe Ser Gly Ser
    50                  55                  60

Gly Ser Gly Thr Ser Tyr Thr Leu Thr Ile Asn Arg Val Glu Ala Glu
65                  70                  75                  80

Asp Ala Ala Thr Tyr Tyr Cys Gln Gln Trp Ser Ser Asn Pro Phe Thr
                85                  90                  95

Phe Gly Gln Gly Thr Lys Leu Glu Ile Lys
            100                 105

<210> SEQ ID NO 22
<211> LENGTH: 121
<212> TYPE: PRT
<213> ORGANISM: Artificial Sequence
<220> FEATURE:
<223> OTHER INFORMATION: humanized mouse IgG

<400> SEQUENCE: 22

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Phe Tyr
            20                  25                  30

Thr Met His Trp Val Arg Gln Ala Pro Gly Gln Gly Leu Glu Trp Ile
        35                  40                  45

Gly Tyr Ile Asn Pro Ser Ser Gly Tyr Thr Asn Tyr Asn Gln Lys Phe
    50                  55                  60

Thr Asp Arg Val Thr Leu Thr Ala Asp Thr Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Asp Gly Ser Ser Ser Lys Trp Tyr Phe Asp Val Trp Gly
            100                 105                 110

Gln Gly Thr Thr Val Thr Val Ser Ser
        115                 120

<210> SEQ ID NO 23
<211> LENGTH: 121
<212> TYPE: PRT
<213> ORGANISM: Artificial Sequence
<220> FEATURE:
<223> OTHER INFORMATION: humanized mouse IgG

<400> SEQUENCE: 23

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Phe Tyr
            20                  25                  30

Thr Met His Trp Leu Arg Gln Ala Pro Gly Gln Gly Leu Glu Trp Ile
        35                  40                  45

Gly Tyr Ile Asn Pro Ser Ser Gly Tyr Thr Asn Tyr Asn Gln Lys Phe
    50                  55                  60

```
Thr Asp Arg Ala Thr Leu Thr Ala Asp Thr Ser Thr Thr Ala Tyr
 65                  70                  75                  80

Met Glu Leu Ser Ser Leu Arg Ser Glu Asp Thr Ala Val Tyr Tyr Cys
                 85                  90                  95

Ala Arg Ser Asp Gly Ser Ser Lys Trp Tyr Phe Asp Val Trp Gly
            100                 105                 110

Gln Gly Thr Thr Val Thr Val Ser Ser
            115                 120

<210> SEQ ID NO 24
<211> LENGTH: 121
<212> TYPE: PRT
<213> ORGANISM: Artificial Sequence
<220> FEATURE:
<223> OTHER INFORMATION: humanized mouse IgG

<400> SEQUENCE: 24

Gln Val Gln Leu Val Gln Ser Gly Ala Glu Val Lys Lys Pro Gly Ala
 1               5                  10                  15

Ser Val Lys Met Ser Cys Lys Ala Ser Gly Tyr Thr Phe Thr Phe Tyr
                 20                  25                  30

Thr Met His Trp Leu Lys Gln Ala Pro Gly Gln Gly Leu Glu Trp Ile
             35                  40                  45

Gly Tyr Ile Asn Pro Ser Ser Gly Tyr Thr Asn Tyr Asn Gln Lys Phe
 50                  55                  60

Thr Asp Arg Ala Thr Leu Thr Ala Asp Thr Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Ser Asp Gly Ser Ser Lys Trp Tyr Phe Asp Val Trp Gly
            100                 105                 110

Gln Gly Thr Thr Val Thr Val Ser Ser
            115                 120

<210> SEQ ID NO 25
<211> LENGTH: 121
<212> TYPE: PRT
<213> ORGANISM: Artificial Sequence
<220> FEATURE:
<223> OTHER INFORMATION: humanized mouse IgG

<400> SEQUENCE: 25

Gln Val Gln Leu Val Gln Ser Gly Ala Glu Val Lys Lys Pro Gly Ala
 1               5                  10                  15

Ser Val Lys Met Ser Cys Lys Ala Ser Gly Tyr Thr Phe Thr Phe Tyr
                 20                  25                  30

Thr Met His Trp Leu Lys Gln Ala Pro Gly Gln Gly Leu Glu Trp Ile
             35                  40                  45

Gly Tyr Ile Asn Pro Ser Ser Gly Tyr Thr Asn Tyr Asn Gln Lys Phe
 50                  55                  60

Thr Asp Arg Ala Thr Leu Thr Ala Asp Lys Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Ser Asp Gly Ser Ser Lys Trp Tyr Phe Asp Val Trp Gly
            100                 105                 110

Gln Gly Thr Thr Val Thr Val Ser Ser
            115                 120
```

<210> SEQ ID NO 26
<211> LENGTH: 10
<212> TYPE: PRT
<213> ORGANISM: Mus musculus

<400> SEQUENCE: 26

Arg Ala Ser Ser Val Ser Tyr Ile His
1               5                   10

<210> SEQ ID NO 27
<211> LENGTH: 7
<212> TYPE: PRT
<213> ORGANISM: Mus musculus

<400> SEQUENCE: 27

Ala Thr Ser Asn Leu Ala Ser
1               5

<210> SEQ ID NO 28
<211> LENGTH: 9
<212> TYPE: PRT
<213> ORGANISM: Mus musculus

<400> SEQUENCE: 28

Gln Gln Trp Ser Ser Asn Pro Phe Thr
1               5

<210> SEQ ID NO 29
<211> LENGTH: 5
<212> TYPE: PRT
<213> ORGANISM: Mus musculus

<400> SEQUENCE: 29

Phe Tyr Thr Met His
1               5

<210> SEQ ID NO 30
<211> LENGTH: 17
<212> TYPE: PRT
<213> ORGANISM: Mus musculus

<400> SEQUENCE: 30

Tyr Ile Asn Pro Ser Ser Gly Tyr Thr Asn Tyr Asn Gln Lys Phe Thr
1               5                   10                  15
Asp

<210> SEQ ID NO 31
<211> LENGTH: 12
<212> TYPE: PRT
<213> ORGANISM: Mus musculus

<400> SEQUENCE: 31

Ser Asp Gly Ser Ser Ser Lys Trp Tyr Phe Asp Val
1               5                   10

<210> SEQ ID NO 32
<211> LENGTH: 443
<212> TYPE: PRT
<213> ORGANISM: Artificial Sequence
<220> FEATURE:
<223> OTHER INFORMATION: humanized mouse Fv, human Fc

<400> SEQUENCE: 32

-continued

```
Glu Val Gln Leu Val Gln Ser Gly Ala Glu Val Lys Lys Pro Gly Ala
1               5                   10                  15

Thr Val Lys Ile Ser Cys Lys Ala Ser Gly Phe Asn Ile Lys Asp Tyr
            20                  25                  30

Tyr Ile His Trp Val Asn Gln Ala Pro Gly Lys Gly Leu Glu Trp Ile
                35                  40                  45

Gly Arg Ile Asp Pro Glu Asp Gly Asp Ile Ala Tyr Ala Pro Lys Phe
        50                  55                  60

Gln Asp Arg Val Thr Leu Thr Val Asp Thr Ser Thr Asp Thr Ala Tyr
65                  70                  75                  80

Leu Glu Leu Ser Ser Leu Arg Ser Glu Asp Thr Ala Val Tyr Tyr Cys
                85                  90                  95

Thr Thr Gly Asn Tyr Tyr Ala Met Asp Phe Trp Gly Gln Gly Thr Thr
            100                 105                 110

Val Thr Val Ser Ser Ala Ser Thr Lys Gly Pro Ser Val Phe Pro Leu
                115                 120                 125

Ala Pro Cys Ser Arg Ser Thr Ser Glu Ser Thr Ala Ala Leu Gly Cys
        130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Asn
            180                 185                 190

Phe Gly Thr Gln Thr Tyr Thr Cys Asn Val Asp His Lys Pro Ser Asn
                195                 200                 205

Thr Lys Val Asp Lys Thr Val Glu Arg Lys Cys Cys Val Glu Cys Pro
        210                 215                 220

Pro Cys Pro Ala Pro Pro Val Ala Gly Pro Ser Val Phe Leu Phe Pro
225                 230                 235                 240

Pro Lys Pro Lys Asp Thr Leu Met Ile Ser Arg Thr Pro Glu Val Thr
                245                 250                 255

Cys Val Val Val Asp Val Ser His Glu Asp Pro Glu Val Gln Phe Asn
            260                 265                 270

Trp Tyr Val Asp Gly Val Glu Val His Asn Ala Lys Thr Lys Pro Arg
                275                 280                 285

Glu Glu Gln Phe Asn Ser Thr Phe Arg Val Val Ser Val Leu Thr Val
        290                 295                 300

Val His Gln Asp Trp Leu Asn Gly Lys Glu Tyr Lys Cys Lys Val Ser
305                 310                 315                 320

Asn Lys Gly Leu Pro Ala Pro Ile Glu Lys Thr Ile Ser Lys Thr Lys
                325                 330                 335

Gly Gln Pro Arg Glu Pro Gln Val Tyr Thr Leu Pro Pro Ser Arg Glu
            340                 345                 350

Glu Met Thr Lys Asn Gln Val Ser Leu Thr Cys Leu Val Lys Gly Phe
        355                 360                 365

Tyr Pro Ser Asp Ile Ala Val Glu Trp Glu Ser Asn Gly Gln Pro Glu
    370                 375                 380

Asn Asn Tyr Lys Thr Thr Pro Pro Met Leu Asp Ser Asp Gly Ser Phe
385                 390                 395                 400

Phe Leu Tyr Ser Lys Leu Thr Val Asp Lys Ser Arg Trp Gln Gln Gly
                405                 410                 415

Asn Val Phe Ser Cys Ser Val Met His Glu Ala Leu His Asn His Tyr
```

```
                        420                 425                 430
Thr Gln Lys Ser Leu Ser Leu Ser Pro Gly Lys
            435                 440

<210> SEQ ID NO 33
<211> LENGTH: 215
<212> TYPE: PRT
<213> ORGANISM: Artificial Sequence
<220> FEATURE:
<223> OTHER INFORMATION: humanized mouse Fv, human constant (Ckappa)

<400> SEQUENCE: 33

Gln Ile Val Leu Thr Gln Ser Pro Ala Thr Leu Ser Ala Ser Pro Gly
1               5                   10                  15

Glu Arg Val Thr Leu Ser Cys Thr Ala Ser Ser Val Ser Ser Ser
            20                  25                  30

Tyr Leu His Trp Tyr Gln Gln Lys Pro Gly Ser Ser Pro Lys Leu Trp
        35                  40                  45

Ile Tyr Ser Thr Ser Asn Leu Ala Ser Gly Val Pro Ala Arg Phe Ser
    50                  55                  60

Gly Ser Gly Pro Gly Thr Ser Tyr Thr Leu Thr Ile Ser Ser Met Glu
65                  70                  75                  80

Pro Glu Asp Ala Ala Thr Tyr Tyr Cys His Gln Tyr His Arg Ser Pro
                85                  90                  95

Pro Thr Phe Gly Gln Gly Thr Lys Leu Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215

<210> SEQ ID NO 34
<211> LENGTH: 443
<212> TYPE: PRT
<213> ORGANISM: Artificial Sequence
<220> FEATURE:
<223> OTHER INFORMATION: humanized mouse Fv, human Fc

<400> SEQUENCE: 34

Glu Val Gln Leu Gln Gln Ser Gly Ala Glu Val Lys Lys Pro Gly Ala
1               5                   10                  15

Thr Val Lys Leu Ser Cys Lys Ala Ser Gly Phe Asn Ile Lys Asp Tyr
            20                  25                  30

Tyr Ile His Trp Val Asn Gln Arg Pro Gly Gln Gly Leu Glu Trp Ile
        35                  40                  45

Gly Arg Ile Asp Pro Glu Asp Gly Asp Ile Ala Tyr Ala Pro Lys Phe
    50                  55                  60
```

Gln Asp Arg Ala Thr Leu Thr Val Asp Thr Ser Thr Asn Thr Ala Tyr
 65                  70                  75                  80

Leu Glu Leu Ser Ser Leu Arg Ser Glu Asp Thr Ala Val Tyr Tyr Cys
                 85                  90                  95

Thr Thr Gly Asn Tyr Tyr Ala Met Asp Phe Trp Gly Gln Gly Thr Thr
            100                 105                 110

Val Thr Val Ser Ser Ala Ser Thr Lys Gly Pro Ser Val Phe Pro Leu
        115                 120                 125

Ala Pro Cys Ser Arg Ser Thr Ser Glu Ser Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Asn
            180                 185                 190

Phe Gly Thr Gln Thr Tyr Thr Cys Asn Val Asp His Lys Pro Ser Asn
        195                 200                 205

Thr Lys Val Asp Lys Thr Val Glu Arg Lys Cys Cys Val Glu Cys Pro
    210                 215                 220

Pro Cys Pro Ala Pro Pro Val Ala Gly Pro Ser Val Phe Leu Phe Pro
225                 230                 235                 240

Pro Lys Pro Lys Asp Thr Leu Met Ile Ser Arg Thr Pro Glu Val Thr
                245                 250                 255

Cys Val Val Val Asp Val Ser His Glu Asp Pro Glu Val Gln Phe Asn
            260                 265                 270

Trp Tyr Val Asp Gly Val Glu Val His Asn Ala Lys Thr Lys Pro Arg
        275                 280                 285

Glu Glu Gln Phe Asn Ser Thr Phe Arg Val Val Ser Val Leu Thr Val
    290                 295                 300

Val His Gln Asp Trp Leu Asn Gly Lys Glu Tyr Lys Cys Lys Val Ser
305                 310                 315                 320

Asn Lys Gly Leu Pro Ala Pro Ile Glu Lys Thr Ile Ser Lys Thr Lys
                325                 330                 335

Gly Gln Pro Arg Glu Pro Gln Val Tyr Thr Leu Pro Pro Ser Arg Glu
            340                 345                 350

Glu Met Thr Lys Asn Gln Val Ser Leu Thr Cys Leu Val Lys Gly Phe
        355                 360                 365

Tyr Pro Ser Asp Ile Ala Val Glu Trp Glu Ser Asn Gly Gln Pro Glu
    370                 375                 380

Asn Asn Tyr Lys Thr Thr Pro Pro Met Leu Asp Ser Asp Gly Ser Phe
385                 390                 395                 400

Phe Leu Tyr Ser Lys Leu Thr Val Asp Lys Ser Arg Trp Gln Gln Gly
                405                 410                 415

Asn Val Phe Ser Cys Ser Val Met His Glu Ala Leu His Asn His Tyr
            420                 425                 430

Thr Gln Lys Ser Leu Ser Leu Ser Pro Gly Lys
        435                 440

<210> SEQ ID NO 35
<211> LENGTH: 106
<212> TYPE: PRT
<213> ORGANISM: Mus musculus

<400> SEQUENCE: 35

-continued

Gln Ile Val Leu Ser Gln Ser Pro Thr Ile Leu Ser Ala Ser Pro Gly
1               5                   10                  15

Glu Lys Val Thr Met Thr Cys Arg Ala Ser Ser Ser Val Ser Tyr Ile
            20                  25                  30

His Trp Tyr Gln Gln Lys Pro Gly Ser Ser Pro Lys Ala Trp Ile Ser
        35                  40                  45

Ala Thr Ser Asn Leu Ala Ser Gly Val Pro Ala Arg Phe Ser Gly Ser
    50                  55                  60

Gly Ser Gly Thr Ser Tyr Ser Leu Thr Ile Ser Arg Val Glu Ala Glu
65                  70                  75                  80

Asp Ala Ala Thr Tyr Tyr Cys Gln Gln Trp Ser Asn Pro Phe Thr
                85                  90                  95

Phe Gly Ser Gly Thr Lys Leu Glu Ile Lys
            100                 105

<210> SEQ ID NO 36
<211> LENGTH: 121
<212> TYPE: PRT
<213> ORGANISM: Mus musculus

<400> SEQUENCE: 36

Gln Val Gln Leu Gln Gln Ser Gly Ala Glu Leu Ala Arg Pro Gly Ala
1               5                   10                  15

Ser Val Lys Met Ser Cys Lys Ala Ser Gly Tyr Thr Phe Thr Phe Tyr
            20                  25                  30

Thr Met His Trp Leu Lys Gln Arg Pro Gly Gln Gly Leu Glu Trp Ile
        35                  40                  45

Gly Tyr Ile Asn Pro Ser Ser Gly Tyr Thr Asn Tyr Asn Gln Lys Phe
    50                  55                  60

Thr Asp Lys Ala Thr Leu Thr Ala Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Ser Asp Gly Ser Ser Ser Lys Trp Tyr Phe Asp Val Trp Gly
            100                 105                 110

Thr Gly Thr Thr Val Thr Val Ser Ser
        115                 120

<210> SEQ ID NO 37
<211> LENGTH: 215
<212> TYPE: PRT
<213> ORGANISM: Artificial Sequence
<220> FEATURE:
<223> OTHER INFORMATION: humanized mouse Fv, human constant (Ckappa)

<400> SEQUENCE: 37

Glu Ile Val Leu Thr Gln Ser Pro Ala Thr Leu Ser Leu Ser Pro Gly
1               5                   10                  15

Glu Arg Val Thr Leu Ser Cys Thr Ala Ser Ser Ser Val Ser Ser Ser
            20                  25                  30

Tyr Leu His Trp Tyr Gln Gln Lys Pro Gly Gln Ser Pro Arg Leu Trp
        35                  40                  45

Ile Tyr Ser Thr Ser Asn Leu Ala Ser Gly Val Pro Ala Arg Phe Ser
    50                  55                  60

Gly Ser Gly Pro Gly Thr Ser Phe Thr Leu Thr Ile Ser Ser Leu Glu
65                  70                  75                  80

```
Pro Glu Asp Phe Ala Val Tyr Tyr Cys His Gln Tyr His Arg Ser Pro
                85                  90                  95

Pro Thr Phe Gly Gln Gly Thr Lys Leu Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215

<210> SEQ ID NO 38
<211> LENGTH: 215
<212> TYPE: PRT
<213> ORGANISM: Artificial Sequence
<220> FEATURE:
<223> OTHER INFORMATION: humanized mouse Fv, human constant (Ckappa)

<400> SEQUENCE: 38

Glu Ile Val Leu Thr Gln Ser Pro Ala Thr Leu Ser Leu Ser Pro Gly
1               5                   10                  15

Glu Arg Val Thr Leu Ser Cys Thr Ala Ser Ser Ser Val Ser Ser Ser
                20                  25                  30

Tyr Leu His Trp Tyr Gln Gln Lys Pro Gly Ser Ser Pro Lys Leu Trp
            35                  40                  45

Ile Tyr Ser Thr Ser Asn Leu Ala Ser Gly Val Pro Ala Arg Phe Ser
        50                  55                  60

Gly Ser Gly Pro Gly Thr Ser Phe Thr Leu Thr Ile Ser Ser Leu Glu
65                  70                  75                  80

Pro Glu Asp Phe Ala Val Tyr Tyr Cys His Gln Tyr His Arg Ser Pro
                85                  90                  95

Pro Thr Phe Gly Gln Gly Thr Lys Leu Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215
```

```
<210> SEQ ID NO 39
<211> LENGTH: 215
<212> TYPE: PRT
<213> ORGANISM: Artificial Sequence
<220> FEATURE:
<223> OTHER INFORMATION: humanized mouse Fv, human constant (Ckappa)

<400> SEQUENCE: 39

Glu Ile Val Leu Thr Gln Ser Pro Ala Thr Leu Ser Leu Ser Pro Gly
1               5                   10                  15

Glu Arg Val Thr Leu Ser Cys Thr Ala Ser Ser Val Ser Ser Ser
            20                  25                  30

Tyr Leu His Trp Tyr Gln Gln Lys Pro Gly Ser Ser Pro Lys Leu Trp
        35                  40                  45

Ile Tyr Ser Thr Ser Asn Leu Ala Ser Gly Val Pro Ala Arg Phe Ser
    50                  55                  60

Gly Ser Gly Pro Gly Thr Ser Tyr Thr Leu Thr Ile Ser Ser Met Glu
65                  70                  75                  80

Pro Glu Asp Phe Ala Val Tyr Tyr Cys His Gln Tyr His Arg Ser Pro
                85                  90                  95

Pro Thr Phe Gly Gln Gly Thr Lys Leu Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215

<210> SEQ ID NO 40
<211> LENGTH: 443
<212> TYPE: PRT
<213> ORGANISM: Artificial Sequence
<220> FEATURE:
<223> OTHER INFORMATION: humanized mouse Fv, human Fc

<400> SEQUENCE: 40

Glu Val Gln Leu Val Gln Ser Gly Ala Glu Val Lys Lys Pro Gly Ala
1               5                   10                  15

Thr Val Lys Leu Ser Cys Lys Ala Ser Gly Phe Asn Ile Lys Asp Tyr
            20                  25                  30

Tyr Ile His Trp Val Asn Gln Ala Pro Gly Lys Gly Leu Glu Trp Ile
        35                  40                  45

Gly Arg Ile Asp Pro Glu Asp Gly Asp Ile Ala Tyr Ala Pro Lys Phe
    50                  55                  60

Gln Asp Arg Ala Thr Leu Thr Val Asp Thr Ser Thr Asn Thr Ala Tyr
65                  70                  75                  80

Leu Glu Leu Ser Ser Leu Thr Ser Glu Asp Thr Ala Val Tyr Tyr Cys
                85                  90                  95
```

Thr Thr Gly Asn Tyr Tyr Ala Met Asp Phe Trp Gly Gln Gly Thr Thr
            100                 105                 110
Val Thr Val Ser Ser Ala Ser Thr Lys Gly Pro Ser Val Phe Pro Leu
        115                 120                 125
Ala Pro Cys Ser Arg Ser Thr Ser Glu Ser Thr Ala Ala Leu Gly Cys
130                 135                 140
Leu Val Lys Asp Tyr Phe Pro Glu Pro Val Thr Val Ser Trp Asn Ser
145                 150                 155                 160
Gly Ala Leu Thr Ser Gly Val His Thr Phe Pro Ala Val Leu Gln Ser
                165                 170                 175
Ser Gly Leu Tyr Ser Leu Ser Ser Val Val Thr Val Pro Ser Ser Asn
            180                 185                 190
Phe Gly Thr Gln Thr Tyr Thr Cys Asn Val Asp His Lys Pro Ser Asn
        195                 200                 205
Thr Lys Val Asp Lys Thr Val Glu Arg Lys Cys Cys Val Glu Cys Pro
    210                 215                 220
Pro Cys Pro Ala Pro Pro Val Ala Gly Pro Ser Val Phe Leu Phe Pro
225                 230                 235                 240
Pro Lys Pro Lys Asp Thr Leu Met Ile Ser Arg Thr Pro Glu Val Thr
                245                 250                 255
Cys Val Val Val Asp Val Ser His Glu Asp Pro Glu Val Gln Phe Asn
            260                 265                 270
Trp Tyr Val Asp Gly Val Glu Val His Asn Ala Lys Thr Lys Pro Arg
        275                 280                 285
Glu Glu Gln Phe Asn Ser Thr Phe Arg Val Val Ser Val Leu Thr Val
    290                 295                 300
Val His Gln Asp Trp Leu Asn Gly Lys Glu Tyr Lys Cys Lys Val Ser
305                 310                 315                 320
Asn Lys Gly Leu Pro Ala Pro Ile Glu Lys Thr Ile Ser Lys Thr Lys
                325                 330                 335
Gly Gln Pro Arg Glu Pro Gln Val Tyr Thr Leu Pro Pro Ser Arg Glu
            340                 345                 350
Glu Met Thr Lys Asn Gln Val Ser Leu Thr Cys Leu Val Lys Gly Phe
        355                 360                 365
Tyr Pro Ser Asp Ile Ala Val Glu Trp Glu Ser Asn Gly Gln Pro Glu
370                 375                 380
Asn Asn Tyr Lys Thr Thr Pro Pro Met Leu Asp Ser Asp Gly Ser Phe
385                 390                 395                 400
Phe Leu Tyr Ser Lys Leu Thr Val Asp Lys Ser Arg Trp Gln Gln Gly
                405                 410                 415
Asn Val Phe Ser Cys Ser Val Met His Glu Ala Leu His Asn His Tyr
            420                 425                 430
Thr Gln Lys Ser Leu Ser Leu Ser Pro Gly Lys
        435                 440

<210> SEQ ID NO 41
<211> LENGTH: 443
<212> TYPE: PRT
<213> ORGANISM: Artificial Sequence
<220> FEATURE:
<223> OTHER INFORMATION: humanized mouse Fv, human Fc

<400> SEQUENCE: 41

Glu Val Gln Leu Gln Gln Ser Gly Ala Glu Val Lys Lys Pro Gly Ala
1               5                   10                  15

```
Thr Val Lys Leu Ser Cys Lys Ala Ser Gly Phe Asn Ile Lys Asp Tyr
         20                  25                  30

Tyr Ile His Trp Val Asn Gln Ala Pro Gly Lys Gly Leu Glu Trp Ile
         35                  40                  45

Gly Arg Ile Asp Pro Glu Asp Gly Asp Ile Ala Tyr Ala Pro Lys Phe
 50                  55                  60

Gln Asp Arg Ala Thr Leu Thr Val Asp Thr Ser Thr Asn Thr Ala Tyr
65                   70                  75                  80

Leu Glu Leu Ser Ser Leu Arg Ser Glu Asp Thr Ala Val Tyr Tyr Cys
                 85                  90                  95

Thr Thr Gly Asn Tyr Tyr Ala Met Asp Phe Trp Gly Gln Gly Thr Thr
             100                 105                 110

Val Thr Val Ser Ser Ala Ser Thr Lys Gly Pro Ser Val Phe Pro Leu
         115                 120                 125

Ala Pro Cys Ser Arg Ser Thr Ser Glu Ser Thr Ala Ala Leu Gly Cys
 130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                 165                 170                 175

Ser Gly Leu Tyr Ser Leu Ser Ser Val Val Thr Val Pro Ser Ser Asn
             180                 185                 190

Phe Gly Thr Gln Thr Tyr Thr Cys Asn Val Asp His Lys Pro Ser Asn
         195                 200                 205

Thr Lys Val Asp Lys Thr Val Glu Arg Lys Cys Cys Val Glu Cys Pro
 210                 215                 220

Pro Cys Pro Ala Pro Pro Val Ala Gly Pro Ser Val Phe Leu Phe Pro
225                 230                 235                 240

Pro Lys Pro Lys Asp Thr Leu Met Ile Ser Arg Thr Pro Glu Val Thr
                 245                 250                 255

Cys Val Val Val Asp Val Ser His Glu Asp Pro Glu Val Gln Phe Asn
             260                 265                 270

Trp Tyr Val Asp Gly Val Glu Val His Asn Ala Lys Thr Lys Pro Arg
         275                 280                 285

Glu Glu Gln Phe Asn Ser Thr Phe Arg Val Val Ser Val Leu Thr Val
 290                 295                 300

Val His Gln Asp Trp Leu Asn Gly Lys Glu Tyr Lys Cys Lys Val Ser
305                 310                 315                 320

Asn Lys Gly Leu Pro Ala Pro Ile Glu Lys Thr Ile Ser Lys Thr Lys
                 325                 330                 335

Gly Gln Pro Arg Glu Pro Gln Val Tyr Thr Leu Pro Pro Ser Arg Glu
             340                 345                 350

Glu Met Thr Lys Asn Gln Val Ser Leu Thr Cys Leu Val Lys Gly Phe
         355                 360                 365

Tyr Pro Ser Asp Ile Ala Val Glu Trp Glu Ser Asn Gly Gln Pro Glu
 370                 375                 380

Asn Asn Tyr Lys Thr Thr Pro Pro Met Leu Asp Ser Asp Gly Ser Phe
385                 390                 395                 400

Phe Leu Tyr Ser Lys Leu Thr Val Asp Lys Ser Arg Trp Gln Gln Gly
                 405                 410                 415

Asn Val Phe Ser Cys Ser Val Met His Glu Ala Leu His Asn His Tyr
             420                 425                 430
```

Thr Gln Lys Ser Leu Ser Leu Ser Pro Gly Lys
            435                 440

<210> SEQ ID NO 42
<211> LENGTH: 443
<212> TYPE: PRT
<213> ORGANISM: Artificial Sequence
<220> FEATURE:
<223> OTHER INFORMATION: 42 humanized mouse Fv, human Fc

<400> SEQUENCE: 42

Glu Val Gln Leu Gln Gln Ser Gly Ala Glu Val Lys Lys Pro Gly Ala
1               5                   10                  15

Thr Val Lys Leu Ser Cys Lys Ala Ser Gly Phe Asn Ile Lys Asp Tyr
            20                  25                  30

Tyr Ile His Trp Val Asn Gln Arg Pro Gly Gln Gly Leu Glu Trp Ile
            35                  40                  45

Gly Arg Ile Asp Pro Glu Asp Gly Asp Ile Ala Tyr Ala Pro Lys Phe
    50                  55                  60

Gln Asp Arg Ala Thr Leu Thr Val Asp Thr Ser Thr Asn Thr Ala Tyr
65                  70                  75                  80

Leu Glu Leu Ser Ser Leu Thr Ser Glu Asp Thr Ala Val Tyr Tyr Cys
                85                  90                  95

Thr Thr Gly Asn Tyr Tyr Ala Met Asp Phe Trp Gly Gln Gly Thr Thr
            100                 105                 110

Val Thr Val Ser Ser Ala Ser Thr Lys Gly Pro Ser Val Phe Pro Leu
        115                 120                 125

Ala Pro Cys Ser Arg Ser Thr Ser Glu Ser Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Asn
            180                 185                 190

Phe Gly Thr Gln Thr Tyr Thr Cys Asn Val Asp His Lys Pro Ser Asn
        195                 200                 205

Thr Lys Val Asp Lys Thr Val Glu Arg Lys Cys Cys Val Glu Cys Pro
    210                 215                 220

Pro Cys Pro Ala Pro Pro Val Ala Gly Pro Ser Val Phe Leu Phe Pro
225                 230                 235                 240

Pro Lys Pro Lys Asp Thr Leu Met Ile Ser Arg Thr Pro Glu Val Thr
                245                 250                 255

Cys Val Val Val Asp Val Ser His Glu Asp Pro Glu Val Gln Phe Asn
            260                 265                 270

Trp Tyr Val Asp Gly Val Glu Val His Asn Ala Lys Thr Lys Pro Arg
        275                 280                 285

Glu Glu Gln Phe Asn Ser Thr Phe Arg Val Val Ser Val Leu Thr Val
    290                 295                 300

Val His Gln Asp Trp Leu Asn Gly Lys Glu Tyr Lys Cys Lys Val Ser
305                 310                 315                 320

Asn Lys Gly Leu Pro Ala Pro Ile Glu Lys Thr Ile Ser Lys Thr Lys
                325                 330                 335

Gly Gln Pro Arg Glu Pro Gln Val Tyr Thr Leu Pro Pro Ser Arg Glu
            340                 345                 350

-continued

Glu Met Thr Lys Asn Gln Val Ser Leu Thr Cys Leu Val Lys Gly Phe
            355                 360                 365

Tyr Pro Ser Asp Ile Ala Val Glu Trp Glu Ser Asn Gly Gln Pro Glu
370                 375                 380

Asn Asn Tyr Lys Thr Thr Pro Pro Met Leu Asp Ser Asp Gly Ser Phe
385                 390                 395                 400

Phe Leu Tyr Ser Lys Leu Thr Val Asp Lys Ser Arg Trp Gln Gln Gly
            405                 410                 415

Asn Val Phe Ser Cys Ser Val Met His Glu Ala Leu His Asn His Tyr
            420                 425                 430

Thr Gln Lys Ser Leu Ser Leu Ser Pro Gly Lys
            435                 440

<210> SEQ ID NO 43
<211> LENGTH: 213
<212> TYPE: PRT
<213> ORGANISM: Artificial Sequence
<220> FEATURE:
<223> OTHER INFORMATION: humanized mouse Fv, human constant (Ckappa)

<400> SEQUENCE: 43

Glu Ile Val Leu Thr Gln Ser Pro Asp Phe Gln Ser Val Thr Pro Lys
1               5                   10                  15

Glu Lys Val Thr Ile Thr Cys Arg Ala Ser Ser Ser Val Ser Tyr Ile
            20                  25                  30

His Trp Tyr Gln Gln Lys Pro Asp Ser Ser Pro Lys Ala Trp Ile Ser
        35                  40                  45

Ala Thr Ser Asn Leu Ala Ser Gly Val Pro Ser Arg Phe Ser Gly Ser
    50                  55                  60

Gly Ser Gly Thr Asp Phe Thr Leu Thr Ile Asn Ser Leu Glu Ala Glu
65                  70                  75                  80

Asp Ala Ala Thr Tyr Tyr Cys Gln Gln Trp Ser Ser Asn Pro Phe Thr
                85                  90                  95

Phe Gly Gln Gly Thr Lys Leu Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210

<210> SEQ ID NO 44
<211> LENGTH: 213
<212> TYPE: PRT
<213> ORGANISM: Artificial Sequence
<220> FEATURE:
<223> OTHER INFORMATION: 44 humanized mouse Fv, human constant (Ckappa)

<400> SEQUENCE: 44

```
Glu Ile Val Leu Thr Gln Ser Pro Asp Phe Gln Ser Ala Thr Pro Lys
1               5                   10                  15

Glu Lys Val Thr Ile Thr Cys Arg Ala Ser Ser Ser Val Ser Tyr Ile
            20                  25                  30

His Trp Tyr Gln Gln Lys Pro Asp Ser Ser Pro Lys Ala Trp Ile Ser
        35                  40                  45

Ala Thr Ser Asn Leu Ala Ser Gly Val Pro Ser Arg Phe Ser Gly Ser
    50                  55                  60

Gly Ser Gly Thr Ser Phe Thr Leu Thr Ile Asn Ser Leu Glu Ala Glu
65                  70                  75                  80

Asp Ala Ala Thr Tyr Tyr Cys Gln Gln Trp Ser Ser Asn Pro Phe Thr
                85                  90                  95

Phe Gly Gln Gly Thr Lys Leu Glu Ile Lys Arg Thr Val Ala Ala Pro
                100                 105                 110

Ser Val Phe Ile Phe Pro Pro Ser Asp Glu Gln Leu Lys Ser Gly Thr
            115                 120                 125

Ala Ser Val Val Cys Leu Leu Asn Asn Phe Tyr Pro Arg Glu Ala Lys
        130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210
```

<210> SEQ ID NO 45
<211> LENGTH: 213
<212> TYPE: PRT
<213> ORGANISM: Artificial Sequence
<220> FEATURE:
<223> OTHER INFORMATION: humanized mouse Fv, human constant (Ckappa)

<400> SEQUENCE: 45

```
Glu Ile Val Leu Thr Gln Ser Pro Asp Phe Gln Ser Ala Thr Pro Lys
1               5                   10                  15

Glu Lys Val Thr Met Thr Cys Arg Ala Ser Ser Ser Val Ser Tyr Ile
            20                  25                  30

His Trp Tyr Gln Gln Lys Pro Asp Ser Ser Pro Lys Ala Trp Ile Ser
        35                  40                  45

Ala Thr Ser Asn Leu Ala Ser Gly Val Pro Ser Arg Phe Ser Gly Ser
    50                  55                  60

Gly Ser Gly Thr Ser Tyr Thr Leu Thr Ile Asn Ser Val Glu Ala Glu
65                  70                  75                  80

Asp Ala Ala Thr Tyr Tyr Cys Gln Gln Trp Ser Ser Asn Pro Phe Thr
                85                  90                  95

Phe Gly Gln Gly Thr Lys Leu Glu Ile Lys Arg Thr Val Ala Ala Pro
                100                 105                 110

Ser Val Phe Ile Phe Pro Pro Ser Asp Glu Gln Leu Lys Ser Gly Thr
            115                 120                 125

Ala Ser Val Val Cys Leu Leu Asn Asn Phe Tyr Pro Arg Glu Ala Lys
        130                 135                 140
```

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210

<210> SEQ ID NO 46
<211> LENGTH: 213
<212> TYPE: PRT
<213> ORGANISM: Artificial Sequence
<220> FEATURE:
<223> OTHER INFORMATION: 46 humanized mouse Fv, human constant (Ckappa)

<400> SEQUENCE: 46

Glu Ile Val Leu Thr Gln Ser Pro Asp Phe Gln Ser Ala Thr Pro Lys
1               5                   10                  15

Glu Lys Val Thr Ile Thr Cys Arg Ala Ser Ser Ser Val Ser Tyr Ile
            20                  25                  30

His Trp Tyr Gln Gln Lys Pro Gly Ser Ser Pro Lys Ala Trp Ile Ser
        35                  40                  45

Ala Thr Ser Asn Leu Ala Ser Gly Val Pro Ser Arg Phe Ser Gly Ser
    50                  55                  60

Gly Ser Gly Thr Ser Tyr Thr Leu Thr Ile Asn Arg Val Glu Ala Glu
65                  70                  75                  80

Asp Ala Ala Thr Tyr Tyr Cys Gln Gln Trp Ser Asn Pro Phe Thr
                85                  90                  95

Phe Gly Gln Gly Thr Lys Leu Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210

<210> SEQ ID NO 47
<211> LENGTH: 447
<212> TYPE: PRT
<213> ORGANISM: Artificial Sequence
<220> FEATURE:
<223> OTHER INFORMATION: humanized mouse Fv, human Fc

<400> SEQUENCE: 47

Gln Val Gln Leu Val Gln Ser Gly Ala Glu Val Lys Lys Pro Gly Ala

-continued

```
1               5                   10                  15
Ser Val Lys Val Ser Cys Lys Ala Ser Gly Tyr Thr Phe Thr Phe Tyr
            20                  25                  30
Thr Met His Trp Val Arg Gln Ala Pro Gly Gln Gly Leu Glu Trp Ile
            35                  40                  45
Gly Tyr Ile Asn Pro Ser Ser Gly Tyr Thr Asn Tyr Asn Gln Lys Phe
            50                  55                  60
Thr Asp Arg Val Thr Leu Thr Ala Asp Thr Ser Thr Ser Thr Ala Tyr
65                  70                  75                  80
Met Glu Leu Ser Ser Leu Arg Ser Glu Asp Thr Ala Val Tyr Tyr Cys
            85                  90                  95
Ala Arg Ser Asp Gly Ser Ser Lys Trp Tyr Phe Asp Val Trp Gly
            100                 105                 110
Gln Gly Thr Thr Val Thr Val Ser Ala Ser Thr Lys Gly Pro Ser
            115                 120                 125
Val Phe Pro Leu Ala Pro Cys Ser Arg Ser Thr Ser Glu Ser Thr Ala
            130                 135                 140
Ala Leu Gly Cys Leu Val Lys Asp Tyr Phe Pro Glu Pro Val Thr Val
145                 150                 155                 160
Ser Trp Asn Ser Gly Ala Leu Thr Ser Gly Val His Thr Phe Pro Ala
            165                 170                 175
Val Leu Gln Ser Ser Gly Leu Tyr Ser Leu Ser Ser Val Val Thr Val
            180                 185                 190
Pro Ser Ser Asn Phe Gly Thr Gln Thr Tyr Thr Cys Asn Val Asp His
            195                 200                 205
Lys Pro Ser Asn Thr Lys Val Asp Lys Thr Val Glu Arg Lys Cys Cys
            210                 215                 220
Val Glu Cys Pro Pro Cys Pro Ala Pro Pro Val Ala Gly Pro Ser Val
225                 230                 235                 240
Phe Leu Phe Pro Pro Lys Pro Lys Asp Thr Leu Met Ile Ser Arg Thr
            245                 250                 255
Pro Glu Val Thr Cys Val Val Val Asp Val Ser His Glu Asp Pro Glu
            260                 265                 270
Val Gln Phe Asn Trp Tyr Val Asp Gly Val Glu Val His Asn Ala Lys
            275                 280                 285
Thr Lys Pro Arg Glu Glu Gln Phe Asn Ser Thr Phe Arg Val Val Ser
            290                 295                 300
Val Leu Thr Val Val His Gln Asp Trp Leu Asn Gly Lys Glu Tyr Lys
305                 310                 315                 320
Cys Lys Val Ser Asn Lys Gly Leu Pro Ala Pro Ile Glu Lys Thr Ile
            325                 330                 335
Ser Lys Thr Lys Gly Gln Pro Arg Glu Pro Gln Val Tyr Thr Leu Pro
            340                 345                 350
Pro Ser Arg Glu Glu Met Thr Lys Asn Gln Val Ser Leu Thr Cys Leu
            355                 360                 365
Val Lys Gly Phe Tyr Pro Ser Asp Ile Ala Val Glu Trp Glu Ser Asn
            370                 375                 380
Gly Gln Pro Glu Asn Asn Tyr Lys Thr Thr Pro Pro Met Leu Asp Ser
385                 390                 395                 400
Asp Gly Ser Phe Phe Leu Tyr Ser Lys Leu Thr Val Asp Lys Ser Arg
            405                 410                 415
Trp Gln Gln Gly Asn Val Phe Ser Cys Ser Val Met His Glu Ala Leu
            420                 425                 430
```

```
His Asn His Tyr Thr Gln Lys Ser Leu Ser Leu Ser Pro Gly Lys
        435                 440                 445

<210> SEQ ID NO 48
<211> LENGTH: 447
<212> TYPE: PRT
<213> ORGANISM: Artificial Sequence
<220> FEATURE:
<223> OTHER INFORMATION: humanized mouse Fv, human Fc

<400> SEQUENCE: 48

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Phe Tyr
            20                  25                  30

Thr Met His Trp Leu Arg Gln Ala Pro Gly Gln Gly Leu Glu Trp Ile
        35                  40                  45

Gly Tyr Ile Asn Pro Ser Ser Gly Tyr Thr Asn Tyr Asn Gln Lys Phe
    50                  55                  60

Thr Asp Arg Ala Thr Leu Thr Ala Asp Thr Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Asp Gly Ser Ser Ser Lys Trp Tyr Phe Asp Val Trp Gly
            100                 105                 110

Gln Gly Thr Thr Val Thr Val Ser Ser Ala Ser Thr Lys Gly Pro Ser
        115                 120                 125

Val Phe Pro Leu Ala Pro Cys Ser Arg Ser Thr Ser Glu Ser Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Asn Phe Gly Thr Gln Thr Tyr Thr Cys Asn Val Asp His
        195                 200                 205

Lys Pro Ser Asn Thr Lys Val Asp Lys Thr Val Glu Arg Lys Cys Cys
    210                 215                 220

Val Glu Cys Pro Pro Cys Pro Ala Pro Pro Val Ala Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Gln Phe Asn Trp Tyr Val Asp Gly Val Glu Val His Asn Ala Lys
        275                 280                 285

Thr Lys Pro Arg Glu Glu Gln Phe Asn Ser Thr Phe Arg Val Val Ser
    290                 295                 300

Val Leu Thr Val Val His Gln Asp Trp Leu Asn Gly Lys Glu Tyr Lys
305                 310                 315                 320

Cys Lys Val Ser Asn Lys Gly Leu Pro Ala Pro Ile Glu Lys Thr Ile
                325                 330                 335

Ser Lys Thr Lys Gly Gln Pro Arg Glu Pro Gln Val Tyr Thr Leu Pro
            340                 345                 350
```

```
Pro Ser Arg Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Met Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
                420                 425                 430

His Asn His Tyr Thr Gln Lys Ser Leu Ser Leu Ser Pro Gly Lys
                435                 440                 445

<210> SEQ ID NO 49
<211> LENGTH: 447
<212> TYPE: PRT
<213> ORGANISM: Artificial Sequence
<220> FEATURE:
<223> OTHER INFORMATION: humanized mouse Fv, human Fc

<400> SEQUENCE: 49

Gln Val Gln Leu Val Gln Ser Gly Ala Glu Val Lys Lys Pro Gly Ala
1               5                   10                  15

Ser Val Lys Met Ser Cys Lys Ala Ser Gly Tyr Thr Phe Thr Phe Tyr
            20                  25                  30

Thr Met His Trp Leu Lys Gln Ala Pro Gly Gln Gly Leu Glu Trp Ile
        35                  40                  45

Gly Tyr Ile Asn Pro Ser Ser Gly Tyr Thr Asn Tyr Asn Gln Lys Phe
    50                  55                  60

Thr Asp Arg Ala Thr Leu Thr Ala Asp Thr Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Asp Gly Ser Ser Ser Lys Trp Tyr Phe Asp Val Trp Gly
            100                 105                 110

Gln Gly Thr Thr Val Thr Val Ser Ser Ala Ser Thr Lys Gly Pro Ser
        115                 120                 125

Val Phe Pro Leu Ala Pro Cys Ser Arg Ser Thr Ser Glu Ser Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Asn Phe Gly Thr Gln Thr Tyr Thr Cys Asn Val Asp His
        195                 200                 205

Lys Pro Ser Asn Thr Lys Val Asp Lys Thr Val Glu Arg Lys Cys Cys
    210                 215                 220

Val Glu Cys Pro Pro Cys Pro Ala Pro Val Ala Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270
```

```
Val Gln Phe Asn Trp Tyr Val Asp Gly Val Glu Val His Asn Ala Lys
            275                 280                 285

Thr Lys Pro Arg Glu Glu Gln Phe Asn Ser Thr Phe Arg Val Val Ser
290                 295                 300

Val Leu Thr Val Val His Gln Asp Trp Leu Asn Gly Lys Glu Tyr Lys
305                 310                 315                 320

Cys Lys Val Ser Asn Lys Gly Leu Pro Ala Pro Ile Glu Lys Thr Ile
                325                 330                 335

Ser Lys Thr Lys Gly Gln Pro Arg Glu Pro Gln Val Tyr Thr Leu Pro
                340                 345                 350

Pro Ser Arg Glu Glu Met Thr Lys Asn Gln Val Ser Leu Thr Cys Leu
            355                 360                 365

Val Lys Gly Phe Tyr Pro Ser Asp Ile Ala Val Glu Trp Glu Ser Asn
370                 375                 380

Gly Gln Pro Glu Asn Asn Tyr Lys Thr Thr Pro Pro Met Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
                420                 425                 430

His Asn His Tyr Thr Gln Lys Ser Leu Ser Leu Ser Pro Gly Lys
            435                 440                 445

<210> SEQ ID NO 50
<211> LENGTH: 447
<212> TYPE: PRT
<213> ORGANISM: Artificial Sequence
<220> FEATURE:
<223> OTHER INFORMATION: humanized mouse Fv, human Fc

<400> SEQUENCE: 50

Gln Val Gln Leu Val Gln Ser Gly Ala Glu Val Lys Lys Pro Gly Ala
1               5                   10                  15

Ser Val Lys Met Ser Cys Lys Ala Ser Gly Tyr Thr Phe Thr Phe Tyr
            20                  25                  30

Thr Met His Trp Leu Lys Gln Ala Pro Gly Gln Gly Leu Glu Trp Ile
        35                  40                  45

Gly Tyr Ile Asn Pro Ser Ser Gly Tyr Thr Asn Tyr Asn Gln Lys Phe
    50                  55                  60

Thr Asp Arg Ala Thr Leu Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Asp Gly Ser Ser Lys Trp Tyr Phe Asp Val Trp Gly
                100                 105                 110

Gln Gly Thr Thr Val Thr Val Ser Ser Ala Ser Thr Lys Gly Pro Ser
            115                 120                 125

Val Phe Pro Leu Ala Pro Cys Ser Arg Ser Thr Ser Glu Ser Thr Ala
130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
                180                 185                 190
```

-continued

```
Pro Ser Ser Asn Phe Gly Thr Gln Thr Tyr Thr Cys Asn Val Asp His
        195                 200                 205
Lys Pro Ser Asn Thr Lys Val Asp Lys Thr Val Glu Arg Lys Cys Cys
    210                 215                 220
Val Glu Cys Pro Pro Cys Pro Ala Pro Pro Val Ala Gly Pro Ser Val
225                 230                 235                 240
Phe Leu Phe Pro Pro Lys Pro Lys Asp Thr Leu Met Ile Ser Arg Thr
                245                 250                 255
Pro Glu Val Thr Cys Val Val Val Asp Val Ser His Glu Asp Pro Glu
            260                 265                 270
Val Gln Phe Asn Trp Tyr Val Asp Gly Val Glu Val His Asn Ala Lys
        275                 280                 285
Thr Lys Pro Arg Glu Glu Gln Phe Asn Ser Thr Phe Arg Val Val Ser
    290                 295                 300
Val Leu Thr Val Val His Gln Asp Trp Leu Asn Gly Lys Glu Tyr Lys
305                 310                 315                 320
Cys Lys Val Ser Asn Lys Gly Leu Pro Ala Pro Ile Glu Lys Thr Ile
                325                 330                 335
Ser Lys Thr Lys Gly Gln Pro Arg Glu Pro Gln Val Tyr Thr Leu Pro
            340                 345                 350
Pro Ser Arg Glu Glu Met Thr Lys Asn Gln Val Ser Leu Thr Cys Leu
        355                 360                 365
Val Lys Gly Phe Tyr Pro Ser Asp Ile Ala Val Glu Trp Glu Ser Asn
    370                 375                 380
Gly Gln Pro Glu Asn Asn Tyr Lys Thr Thr Pro Pro Met Leu Asp Ser
385                 390                 395                 400
Asp Gly Ser Phe Phe Leu Tyr Ser Lys Leu Thr Val Asp Lys Ser Arg
                405                 410                 415
Trp Gln Gln Gly Asn Val Phe Ser Cys Ser Val Met His Glu Ala Leu
            420                 425                 430
His Asn His Tyr Thr Gln Lys Ser Leu Ser Leu Ser Pro Gly Lys
        435                 440                 445
```